United States Patent
Zhang et al.

(10) Patent No.: US 11,183,643 B2
(45) Date of Patent: Nov. 23, 2021

(54) NITROGEN HETEROCYCLE FUSED RING-INDENE COMPOUND AND ORGANIC LIGHT-EMITTING DISPLAY DEVICE

(71) Applicant: Shanghai Tianma AM-OLED Co., Ltd., Shanghai (CN)

(72) Inventors: Lei Zhang, Shanghai (CN); Xiangcheng Wang, Shanghai (CN); Wei Gao, Shanghai (CN); Jinghua Niu, Shanghai (CN); Ying Liu, Shanghai (CN); Gaojun Huang, Shanghai (CN); Ping An, Shanghai (CN); Xueqiang Luo, Shanghai (CN)

(73) Assignee: SHANGHAI TIANMA AM-OLED CO., LTD., Shanghai (CN)

( * ) Notice: Subject to any disclaimer, the term of this patent is extended or adjusted under 35 U.S.C. 154(b) by 362 days.

(21) Appl. No.: 16/212,292

(22) Filed: Dec. 6, 2018

(65) Prior Publication Data
US 2020/0035929 A1    Jan. 30, 2020

(30) Foreign Application Priority Data
Jul. 26, 2018    (CN) .......................... 201810833396.6

(51) Int. Cl.
*H01L 51/00*    (2006.01)
*C07D 401/10*    (2006.01)
(Continued)

(52) U.S. Cl.
CPC ........ *H01L 51/0072* (2013.01); *C07D 241/38* (2013.01); *C07D 401/10* (2013.01);
(Continued)

(58) Field of Classification Search
CPC .................. H01L 51/0072; H01L 51/0071
See application file for complete search history.

(56) References Cited

U.S. PATENT DOCUMENTS

2011/0031482 A1* 2/2011 Furukawa ........... H01L 51/0072
257/40

FOREIGN PATENT DOCUMENTS

CN    103819415 A    5/2014
CN    106206999 A    12/2016
(Continued)

OTHER PUBLICATIONS

First Office Action for Chinese Patent Application No. 201810833396.6, dated Sep. 4, 2019. (15 pages).
(Continued)

*Primary Examiner* — Jennifer A Boyd
*Assistant Examiner* — Sean M DeGuire
(74) *Attorney, Agent, or Firm* — Christensen O'Connor Johnson Kindness PLLC

(57) ABSTRACT

The present disclosure relates to a nitrogen heterocycle fused ring-indene compound having a structure represented by the Formula (I),

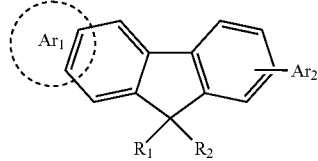

Formula (I)

in which $Ar_1$ represents a substituted or unsubstituted aromatic fused ring group containing at least one nitrogen heteroaryl; $Ar_2$ represents a chemical group acting as an electron donor; $R_1$ and $R_2$ are independently selected from the group consisting of hydrogen, substituted or unsubstituted C1-C20 alkyl, substituted or unsubstituted C3-C20
(Continued)

cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl. The compounds according to the present disclosure have high glass transition temperature and thermal stability, and are easy to form a high-quality amorphous film, so that a driving voltage can be lowered, the luminous efficiency and lifetime of the device are improved.

18 Claims, 2 Drawing Sheets

(51) Int. Cl.
    *C07D 403/10* (2006.01)
    *C07D 471/04* (2006.01)
    *C07D 495/04* (2006.01)
    *C07D 417/04* (2006.01)
    *C07D 413/04* (2006.01)
    *C07D 403/04* (2006.01)
    *C07D 241/38* (2006.01)
    *C07D 491/048* (2006.01)
    *H01L 51/50* (2006.01)

(52) U.S. Cl.
    CPC ......... *C07D 403/04* (2013.01); *C07D 403/10* (2013.01); *C07D 413/04* (2013.01); *C07D 417/04* (2013.01); *C07D 471/04* (2013.01); *C07D 491/048* (2013.01); *C07D 495/04* (2013.01); *H01L 51/0071* (2013.01); *H01L 51/5004* (2013.01); *H01L 51/5016* (2013.01); *H01L 51/5056* (2013.01); *H01L 51/5072* (2013.01); *H01L 2251/552* (2013.01)

(56) References Cited

FOREIGN PATENT DOCUMENTS

| | | | |
|---|---|---|---|
| CN | 106898702 A | | 6/2017 |
| KR | 20120052499 A | * | 5/2012 |
| KR | 20120116879 A | * | 10/2012 |
| KR | 1020170139895 A | | 12/2017 |

OTHER PUBLICATIONS

Hao, Zeng-Shuai et al., "Synthesis, optical, and electrochemical properties of 2,3-diphenyl-10H-indeno[1,2-g]quinoxaline, 15H-dibenzo[a,c]indeno[1,2-i]phenazine, and 15H-indeno[1,2-i]phenanthro[4,5-abc]phenazine derivatives," Dyes and Pigments, 109:54-66, 2014.

Lin, Tzu-Chau, et al., "Two- and three-photon absorption properties of fan-shaped dendrons derived from 2,3,8-trifunctionalized indenoquinoxaline units: synthesis and characterization," Journal of Materials Chemistry C, 5:8219-8232, 2017.

* cited by examiner

NITROGEN HETEROCYCLE FUSED RING-INDENE COMPOUND AND ORGANIC LIGHT-EMITTING DISPLAY DEVICE

CROSS-REFERENCE TO RELATED APPLICATIONS

The present disclosure claims priority to Chinese Patent Application No. 201810833396.6, filed on Jul. 26, 2018, the content of which is incorporated herein by reference in its entirety.

TECHNICAL FIELD

The present disclosure relates to the field of electroluminescence, and in particular, to an electroluminescent material, and use of the electroluminescent material in an organic electroluminescent display device.

BACKGROUND

As a new generation of display technology, organic electroluminescent materials, such as organic light-emitting diodes (OLED) have been widely used in flat-panel displays, flexible displays, solid-state lighting and vehicle displays, due to their advantageous low thickness, self-luminousity, wide viewing angle, fast response, high efficiency, good temperature adaptability, simple manufacturing process, low driving voltage, low energy consumption and the like.

Electroluminescence can be classified into electrofluorescence and electrophosphorescence depending upon the luminescence mechanism. Fluorescence is a result of a radiation attenuation transition of singlet excitons, and phosphorescence is a result of light emitted during attenuation transition to the ground state of triplet excitons. According to the sping-statistics theory, a probability ratio of forming singlet excitons and triplet excitons is 1:3. The internal quantum efficiency of the electrofluorescent material is no more than 25%, and the external quantum efficiency is generally less than 5%. Theoretically, the internal quantum efficiency of the electrophosphorescent material can reach 100%, and the external quantum efficiency can be up to 20%. In 1998, Professor Yuguang Ma from Jilin University in China and Professor Forrest from Princeton University in the United States both have reported that ruthenium complexes and platinum complexes were used as dyes doped into the light-emitting layer, a phenomenon of electrophosphorescence was explained, and applied the prepared phosphorescent material to an electroluminescent device.

The long lifetime (μs) of phosphorescent heavy metal materials may lead to triplet state-triplet state quenching and concentration quenching at high current densities and further result in a degradation of device performance. Therefore, phosphorescent heavy metal materials are usually doped into suitable host materials to form a host-guest doping system. In this way, energy transfer is enhanced, and luminous efficiency and lifetime are increased. At present, heavy metal doping materials have been commercialized, and however, development of alternative doping materials has proven challenging. Thus, developing a novel phosphorescent host material is becoming more and more urgent.

SUMMARY

The present disclosure provides a series of organic compounds having a nitrogen (N) heterocycle fused ring-indene structure as the main skeleton. Such organic compounds have high glass transition temperature and thermal stability, and are easy to form high-quality amorphous films, so that a driving voltage can be lowered, and the luminous efficiency and lifetime of the device are improved. In this regard, the organic compounds of the present disclosure are suitable to be applied to electroluminescent devices.

Specifically, the present disclosure provides a nitrogen heterocycle fused ring-indene compound, having a chemical structure represented by Formula (I):

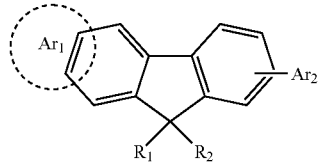

Formula (I)

in which $Ar_1$ is an electron acceptor, and is a substituted or unsubstituted aromatic fused ring group containing at least one nitrogen heteroaryl, the substituted aromatic fused ring group containing at least one nitrogen heteroaryl has one or more substituents each selected from the group consisting of alkyl, alkoxy, heterocyclyl, and aryl;

$Ar_2$ is an electron donor; and $R_1$ and $R_2$ are each independently selected from the group consisting of hydrogen atom, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl. In an embodiment, $R_1$ and $R_2$ are each methyl.

In another aspect, the present disclosure also provides an organic light-emitting display device. The organic light-emitting display device includes an anode, a cathode, and a light-emitting layer disposed between the anode and the cathode. A host material or a guest material of the light-emitting layer is selected from a group consisting of nitrogen heterocycle fused ring-indene compounds according to the present disclosure, and combinations thereof.

DESCRIPTION OF EMBODIMENTS

Figure 1:
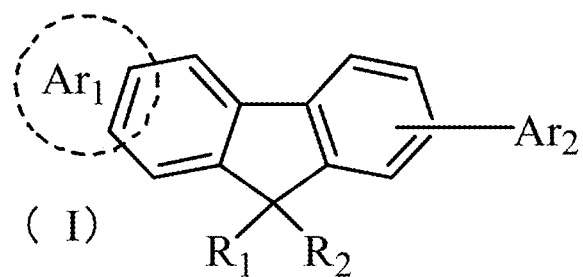
FIG. 1 is a chemical formula of a nitrogen heterocycle fused ring-indene compound according to an embodiment of the present disclosure.

The technical solutions of the present disclosure are described below by means of several specific compounds.

A first aspect of the present disclosure provides a nitrogen heterocycle fused ring-indene compound, having a chemical structure represented by Formula (I):

Formula (I)

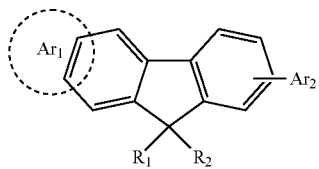

in which $Ar_1$ is an electron acceptor, and is a substituted or unsubstituted aromatic fused ring group containing at least one nitrogen heteroaryl, the substituted aromatic fused ring group containing at least one nitrogen heteroaryl having one or more substituents each selected from the group consisting of alkyl, alkoxy, heterocyclyl, and aryl;

$Ar_2$ is an electron donor; and $R_1$ and $R_2$ are each independently selected from the group consisting of hydrogen atom, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl. In an embodiment, $R_1$ and $R_2$ each is methyl.

According to an embodiment of the present disclosure, the nitrogen heterocycle fused ring-indene compound is any one of following compounds:

I-1

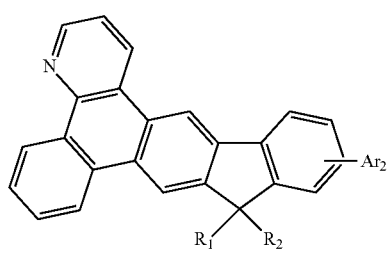

I-2

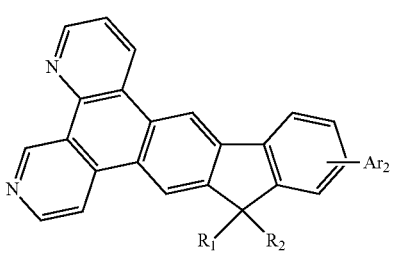

I-3

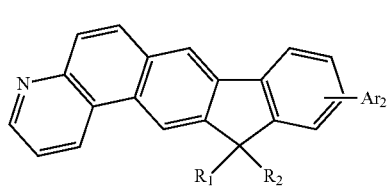

I-4

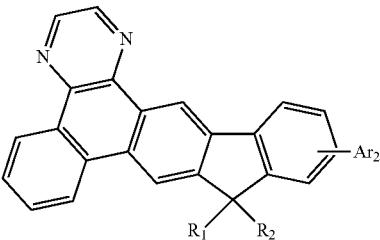

I-5

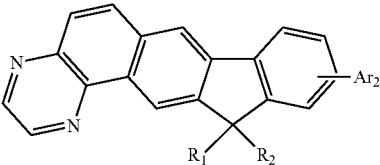

I-6

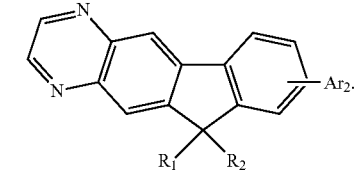

According to an embodiment of the present disclosure, $Ar_2$ is selected from the group consisting of substituted or unsubstituted C1-C20 alkyl, substituted or unsubstituted silicylene, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

According to an embodiment of the present disclosure, $Ar_2$ is any one of following groups:

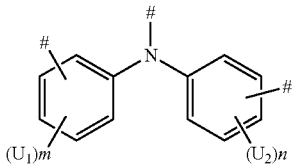

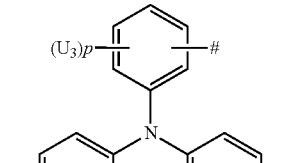

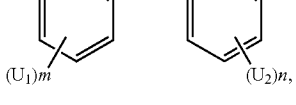

in which m, n and p are each integers independently selected from 0, 1, 2 and 3;

$U_1$, $U_2$ and $U_3$ are each independently selected from the group consisting of hydrogen, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl; and # indicates a bonding position to which a benzene ring in the Formula (I) is bonded.

According to an embodiment of the present disclosure, $Ar_2$ is any one of following groups:

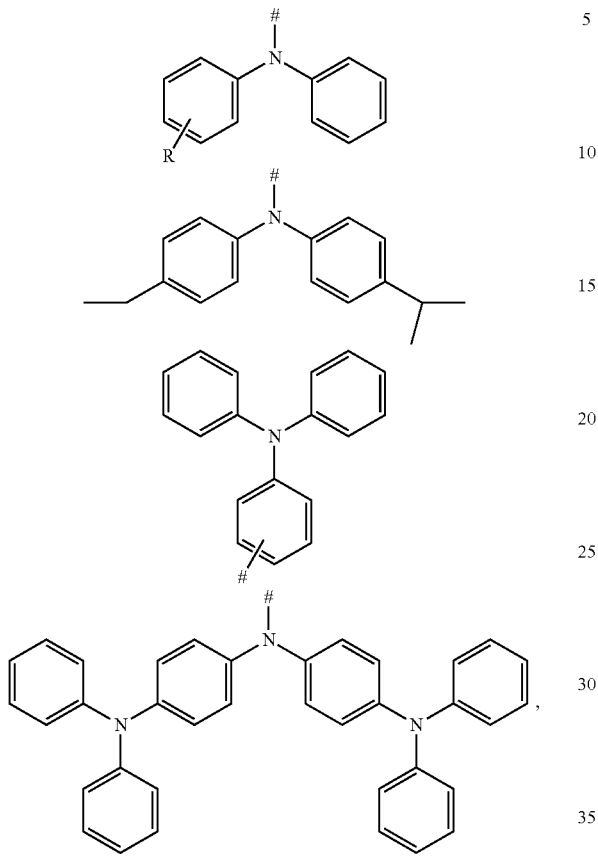

in which R is selected from the group consisting of hydrogen atom, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl.

Diphenylamino group or its derivative, as electron donor A, has a relatively strong electron-donating ability, which is in between the donating ability of carbazolyl and the donating ability of acridinyl, and has a structure with large steric hindrance. In this regard, the diphenylamino structure exhibits a small energy difference between energy levels and a large external quantum efficiency. The diphenylamino group or its derivative also has an intermediate bandgap between carbazole and aniline, so that the emission spectrum shows a green light emission in combination with the electron acceptor according to the present disclosure.

According to an embodiment of the present disclosure, $Ar_2$ is any one of following groups:

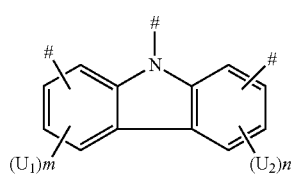

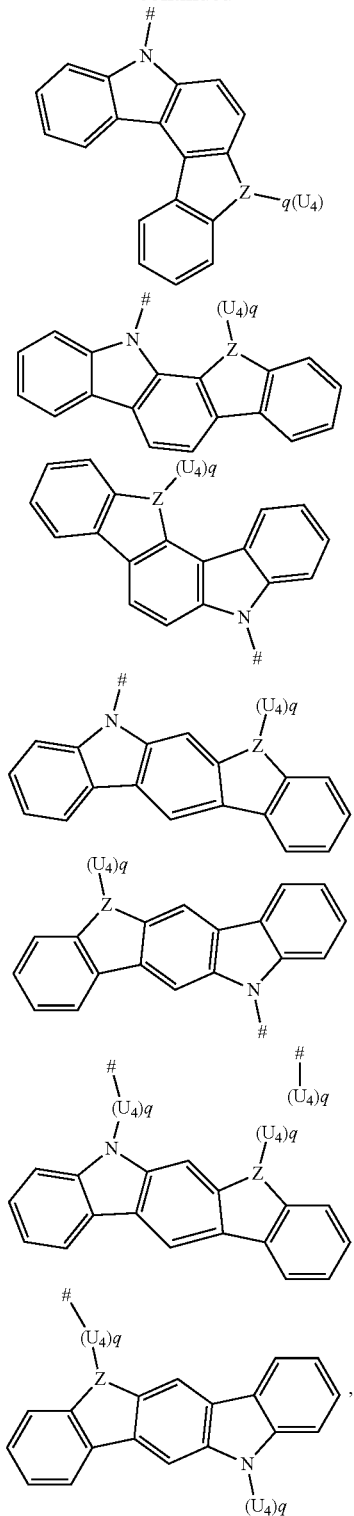

in which Z is selected from the group consisting of carbon, nitrogen, oxygen, sulfur, and silicon;

q is an integer selected from 0, 1, 2 and 3;

$U_4$ is selected from the group consisting of hydrogen, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl;
when Z is an oxygen atom or a sulfur atom, q=0; and
# indicates a bonding position to which a benzene ring in the Formula (I) is bonded.
According to an embodiment of the present disclosure, $Ar_2$ is any one of following groups:
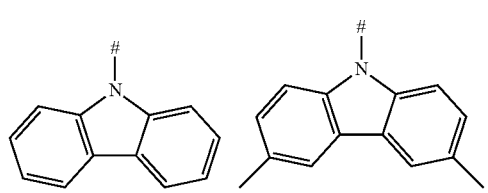
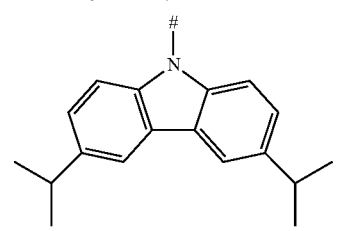
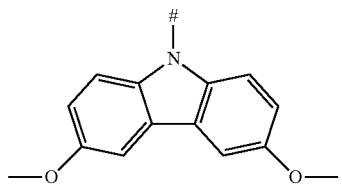
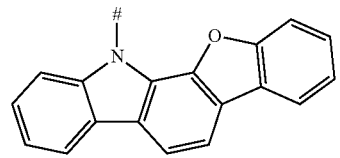
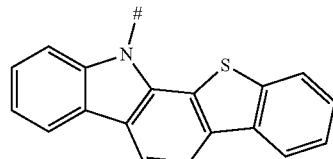
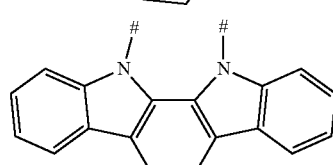
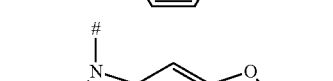
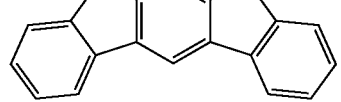
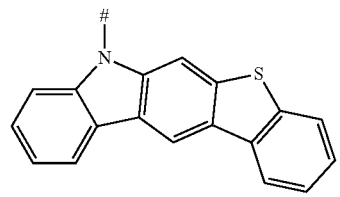
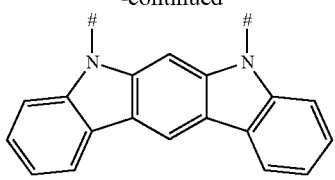
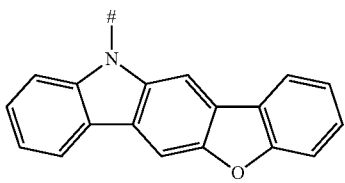
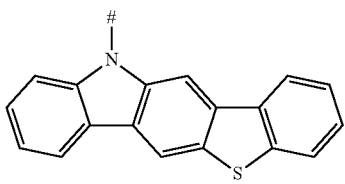
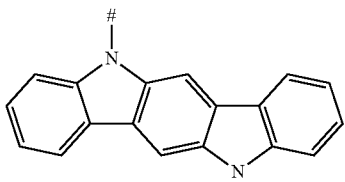
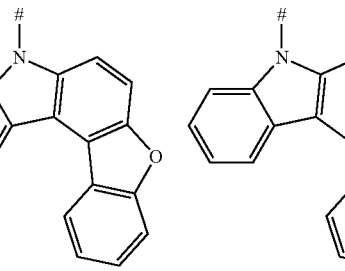
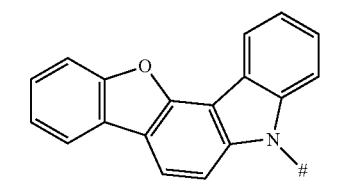
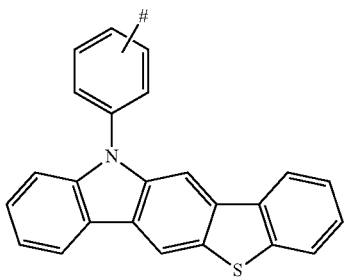

-continued

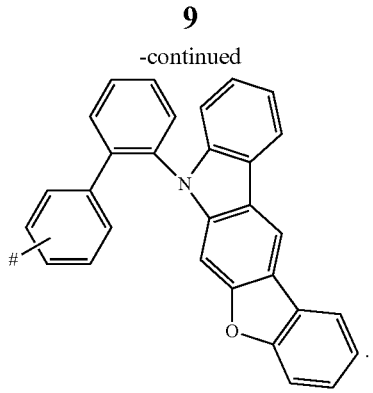

Electron donating groups based on carbazolyl have a relatively weak electron donating ability. In combination with an electron accepting group having strong electron-accepting ability according to the present disclosure, an energy difference between HOMO and LUMO may be relatively large. The band gap also may be relatively wide, and, in this regard, the emission spectrum shows a blue light emission. Meanwhile, the substituents on the derivatives of carbazolyl are fused with another ring, which may result in a higher degree of conjugation. In this way, the structure will have a large steric hindrance, and thus the molecules have a better luminescence performance.

According to an embodiment of the present disclosure, $Ar_2$ is any one of following groups:

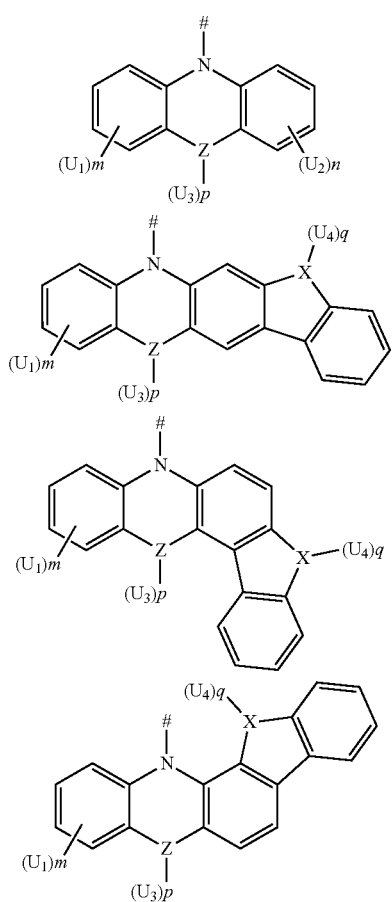

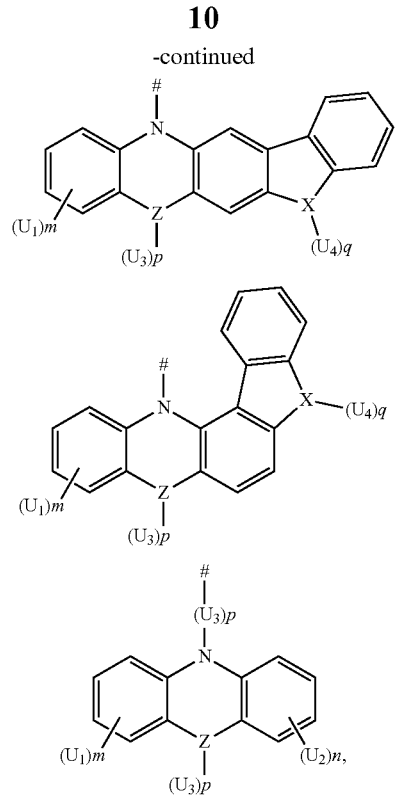

in which Z is selected from the group consisting of carbon, nitrogen, oxygen, sulfur, and silicon;

X is selected from the group consisting of carbon, nitrogen, oxygen, and sulfur;

m, n, p and q are integers independently selected from 0, 1, 2 and 3;

$U_1$, $U_2$, $U_3$ and $U_4$ are each independently selected from the group consisting of hydrogen atom, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl;

when Z or X is oxygen or sulfur, p or q is 0; and # indicates a bonding position to which a benzene ring in the Formula (I) is bonded.

According to an embodiment of the present disclosure, $Ar_2$ is any one of following groups:

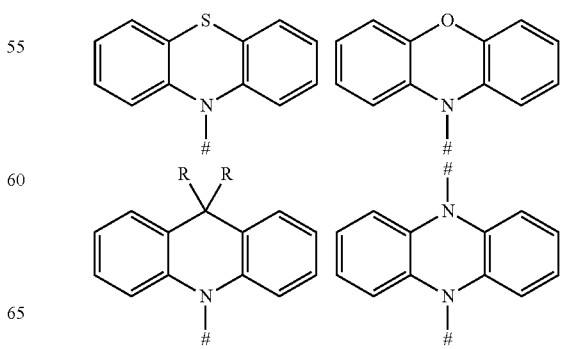

-continued

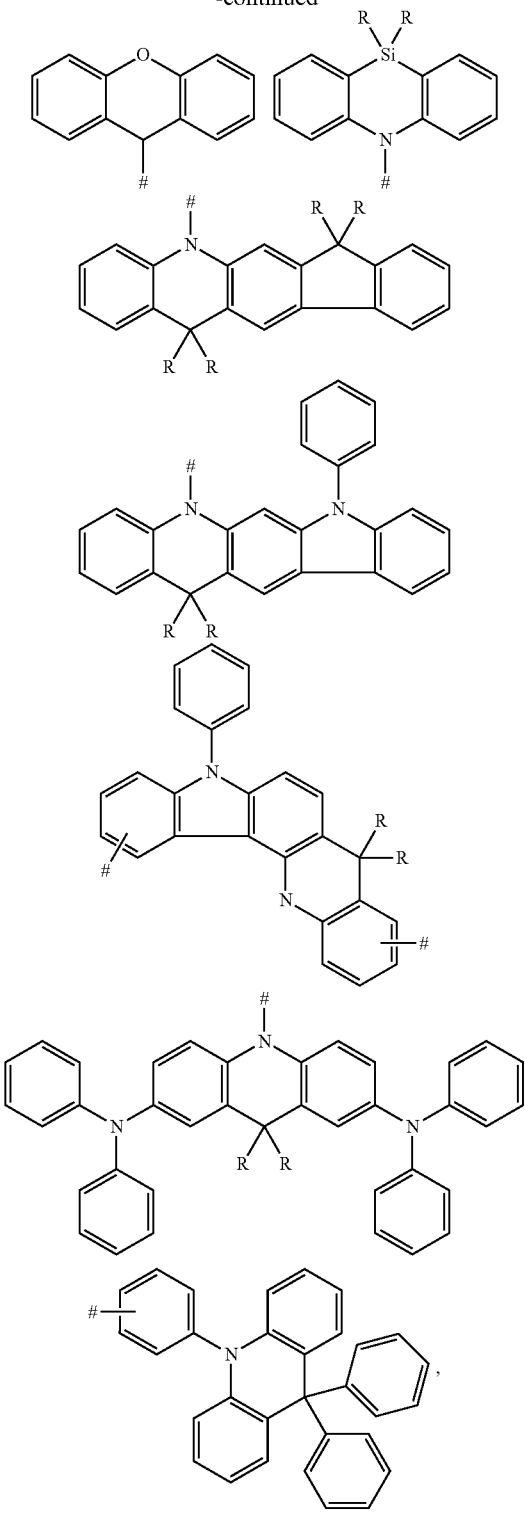

in which R is selected from the group consisting of hydrogen, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

Electron donating groups based on acridinyl have excellent electron donating ability. The electron donating ability of such acridinyl groups can be altered by changing Z atom in the group, which is conducive to adjusting the light-emitting position. The band gap is narrower than the band gap of the carbazoles and anilines, and, in combination with the electron accepting group according to the present disclosure, the emission spectrum shows a red light emission.

According to an embodiment of the present disclosure, $Ar_2$ is any one of following groups:

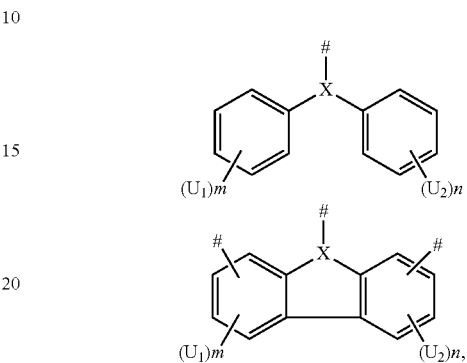

in which X is selected from a group consisting of oxygen, sulfur, and silicon;

m and n are integers independently selected from 0, 1, 2 and 3;

$U_1$ and $U_2$ are each independently selected from the group consisting of hydrogen, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl; and # indicates a bonding position to which a benzene ring in the Formula (I) is bonded.

According to an embodiment of the present disclosure, $Ar_2$ is any one of following groups:

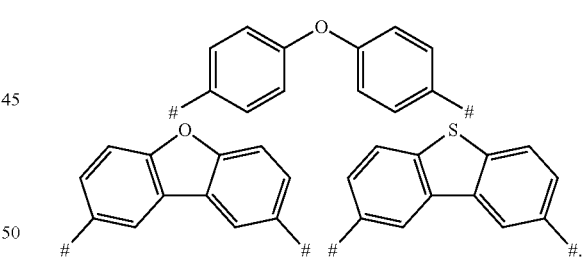

The derivatives of diphenyl ether have relatively strong electron donating ability, and have a structure with a large steric hindrance, so that the structure exhibits a small energy level difference, a large external quantum efficiency, an intermediate band gap located between the band gaps of carbazole and the aniline. In combination with the electron accepting group according to the present disclosure, the emission spectrum shows a green light emission.

The electron donating groups based on oxygen or sulfur heterocyclic derivatives of carbazole do not have strong electron donating ability. In combination with the electron accepting group having strong electron accepting ability according to the present disclosure, the energy difference between HOMO and LUMO is relatively large, and the band gap is relatively wide. The emission spectrum shows a blue light emission. Meanwhile, those substituents are fused with another ring, which results in a higher degree of conjugation. Such structure has a large steric hindrance, so that the molecule has a better luminescence performance.
According to another embodiment of the present disclosure, $Ar_2$ is any one of following group:
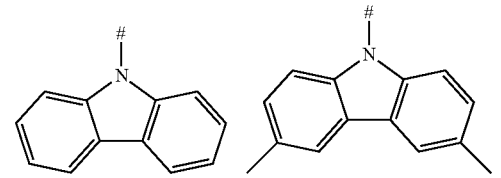
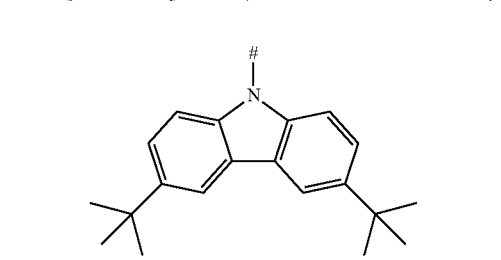
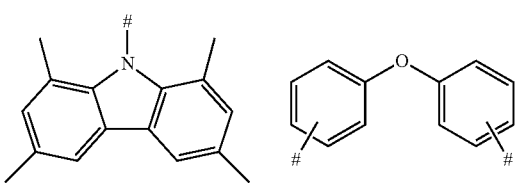
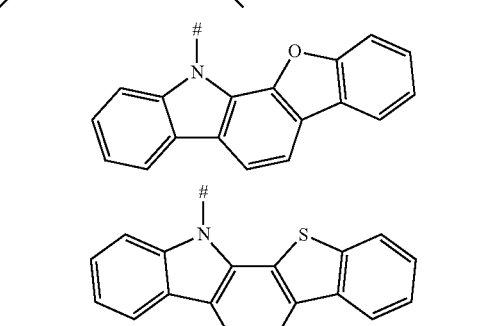
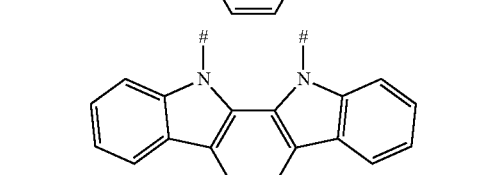
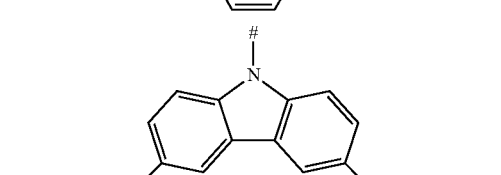
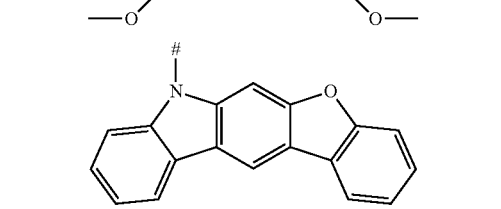
-continued
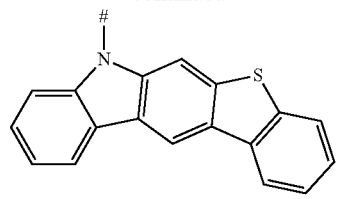
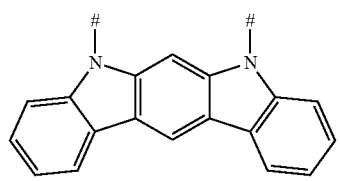
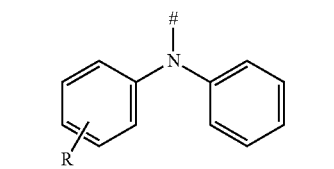
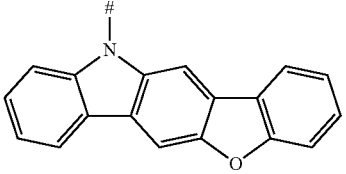
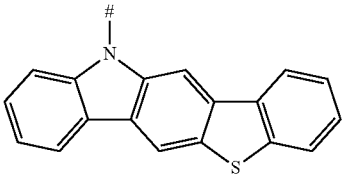
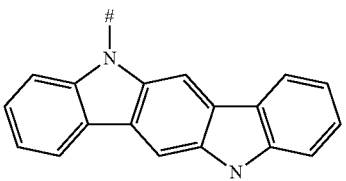
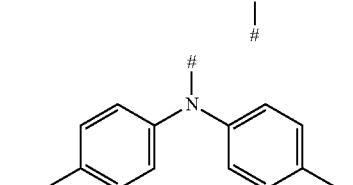
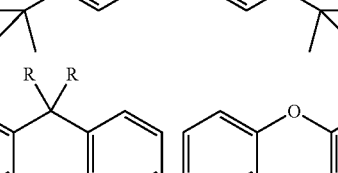
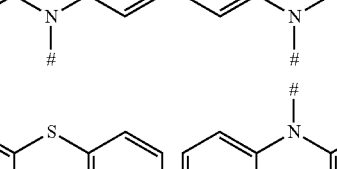
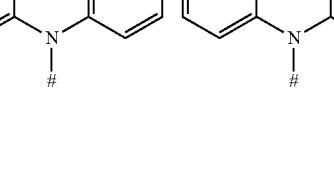

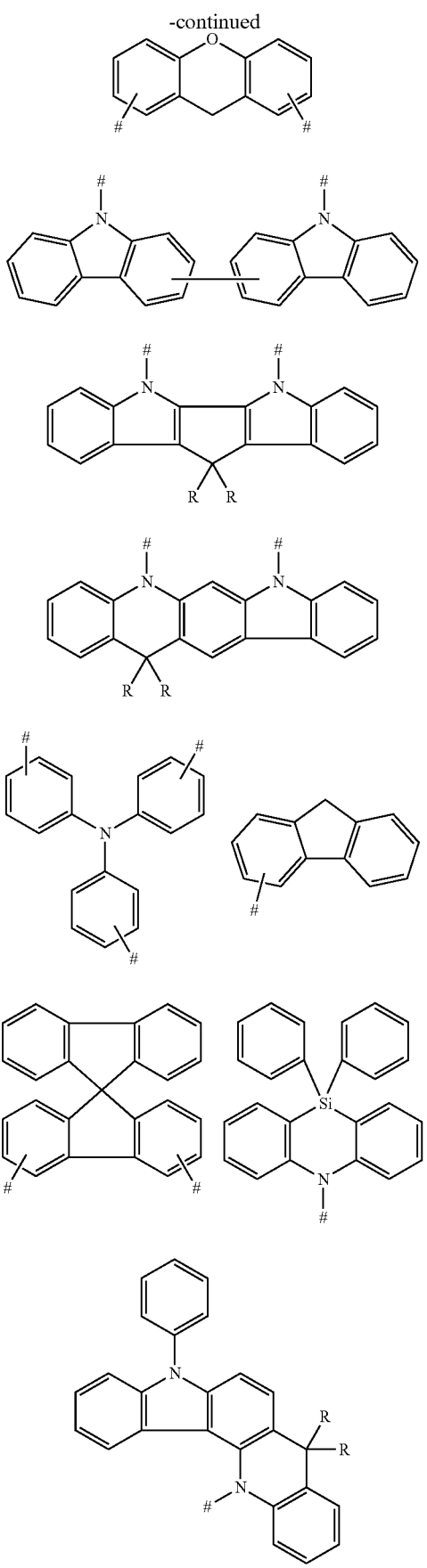
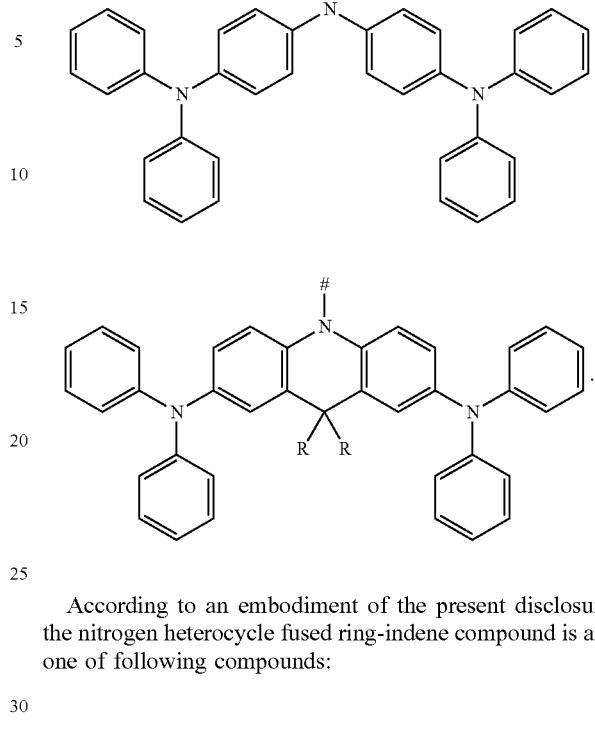
According to an embodiment of the present disclosure, the nitrogen heterocycle fused ring-indene compound is any one of following compounds:
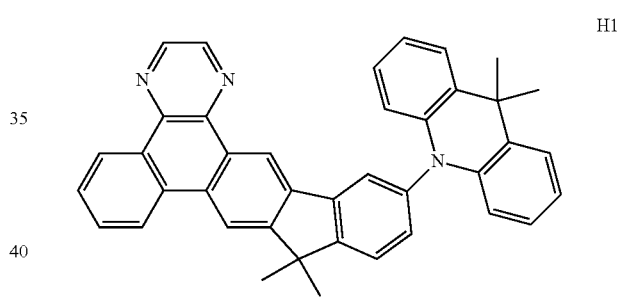
H1
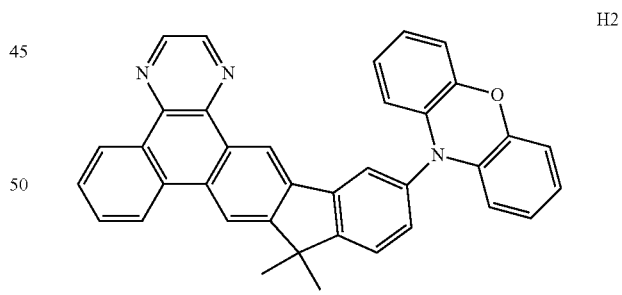
H2
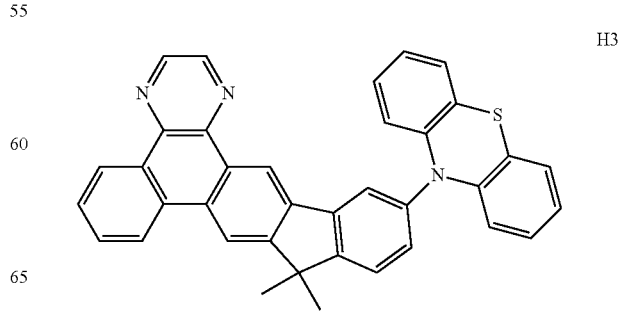
H3

H4
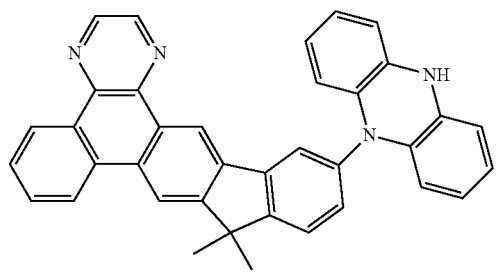
H5
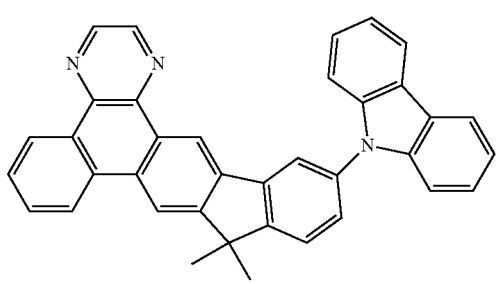
H6
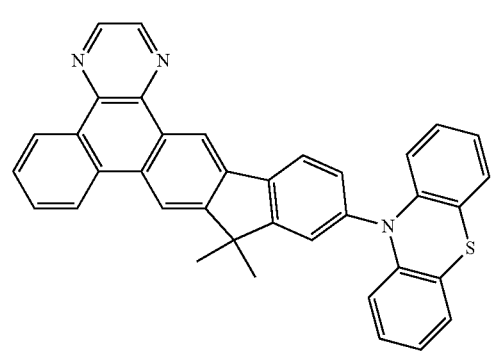
H7
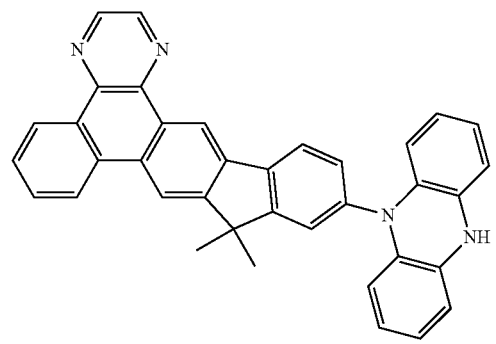
H8
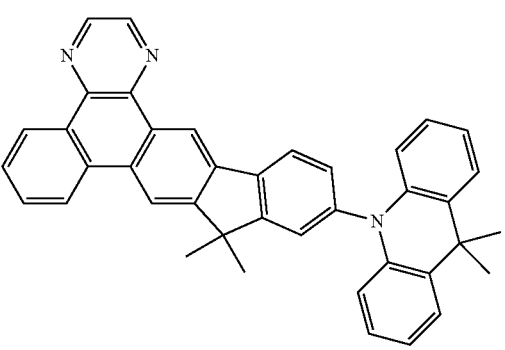
H9
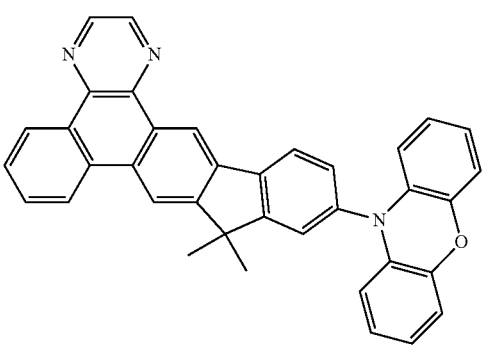
H10
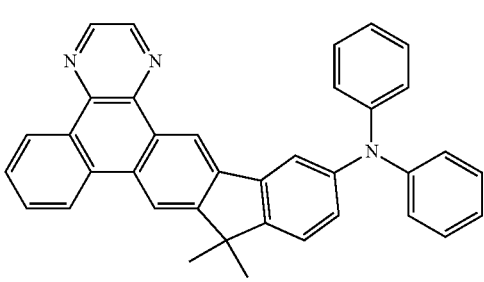
H11
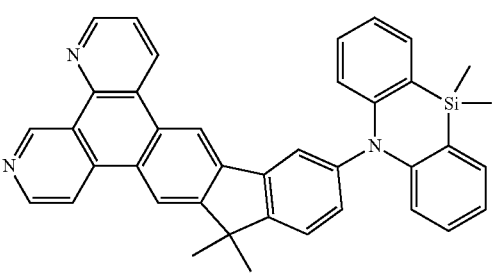
H12
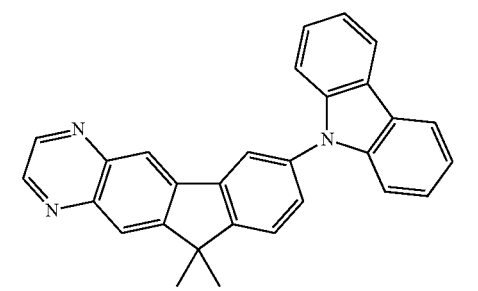
H13
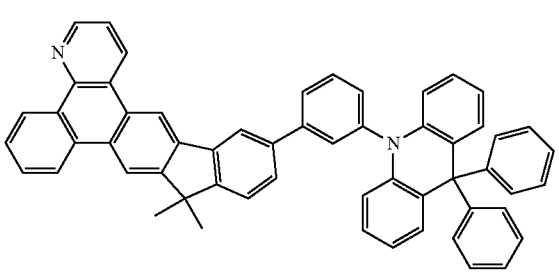

-continued

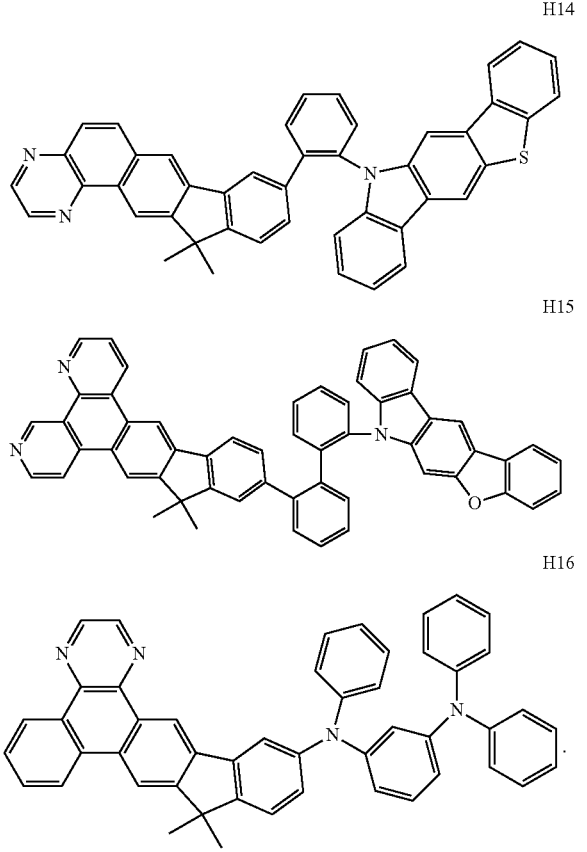

H14

H15

H16

The phosphorescent host material provided by the present disclosure has one or more of the following characteristics:

(1) The triplet energy level $E_T$ of the host material according to the present disclosure is higher than the triplet energy level $E_T$ of the phosphorescent guest material, so that a backflow of the triplet energy from the guest to the host is avoided, thereby limiting the triplet excitons in the light-emitting layer to a maximal extent.

(2) HOMO energy level and LUMO energy level of the host material according to the present disclosure is matched with the energy levels of the material of its adjacent layers, so as to reduce potential barrier of injecting holes and electrons and reduce driving voltage of the device. In addition, an energy difference Eg between HOMO energy level and LUMO energy level of the host material is greater than an energy difference between the energy levels of the phosphorescent guest material, which is conducive to transferring energy from the host material to the guest material and direct capturing current carriers on the phosphorescent guest material.

(3) The host material according to the present disclosure has a relatively high current carrier transmission rate and a balanced carrier transmission performance, so that the hole and electron transmission in the component can be balanced while obtaining a wider carrier recombination region, thereby improving luminescence efficiency.

(4) The host material according to the present disclosure has good thermal stability and film forming property, and the glass transition temperature Tg should be moderately centered, not be too high or too low, so as to form a stable and uniform film and reduce phase separation during the thermal vacuum vapor deposition process. Therefore, the stability of the component is maintained.

The present disclosure provides a series of nitrogen heterocycle fused ring-indene compounds as electron accepting group. These organic compounds can be used as a host material or a capping layer (CPL) material in an electroluminescent component, since they have a high triplet energy level $E_T$, high molecular density, high polarizability, high glass transition temperature and molecular thermal stability. In this way, a balanced migration of current carriers and light extraction efficiency can be effectively improved, and the exciton recombination region can be widened, so that the luminous efficiency and longevity of the device have been significantly improved, and can be well applied in the technical field of electroluminescent component.

The nitrogen heterocycle fused ring-indene compound according to the present disclosure can be used as a light-emitting layer of an organic light-emitting display device, in particular, as a CPL of an organic film layer, as a host material, a dopant or materials of an electron transmission layer or a hole transmission layer.

The present disclosure also provides a method for manufacturing several exemplary nitrogen heterocycle fused ring-indene compounds, as described in Examples 1-5.

Example 1

Synthesis of Compound H1

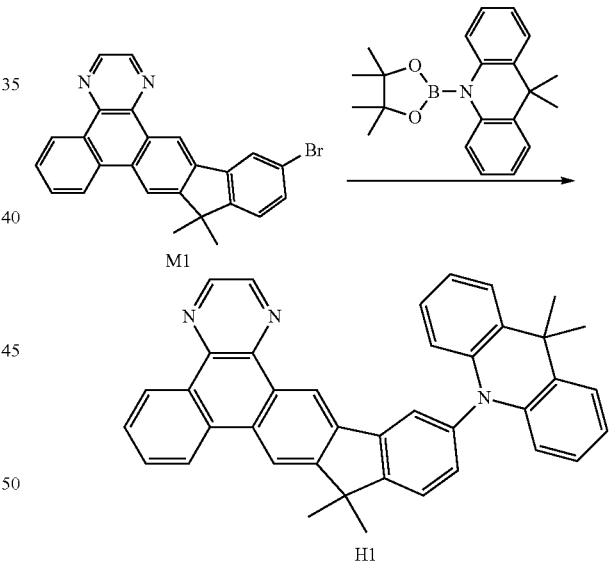

In nitrogen atmosphere, an intermediate Compound M1 (0.012 mol), phenazine borate (0.012 mol), palladium acetate (0.0003 mol) and 150 ml DMF were added in a 250 ml round bottom flask, mixed and stirred. After a solution of $K_3PO_4$ (0.045 mol) in water was added, the mixture was refluxed for 10 h at a temperature of 130° C., then naturally cooled to room temperature, and the mixture was filtered and dried in a vacuum oven after adding 100 ml of water. The obtained crude product was further separated and purified through a silica gel column chromatography to obtain Compound H1.

Elemental analysis of the Compound H1 (Molecular Formula $C_{40}H_{31}N_3$): theoretical values: C, 86.77; H, 5.64;

N, 7.59; test value: C, 86.77; H, 5.65; N, 7.58. The ESI-MS (m/z) (M+) was obtained by liquid chromatography-mass spectrometry: theoretical value: 553.25, and test value: 553.30.

Example 2

Synthesis of Compound H5

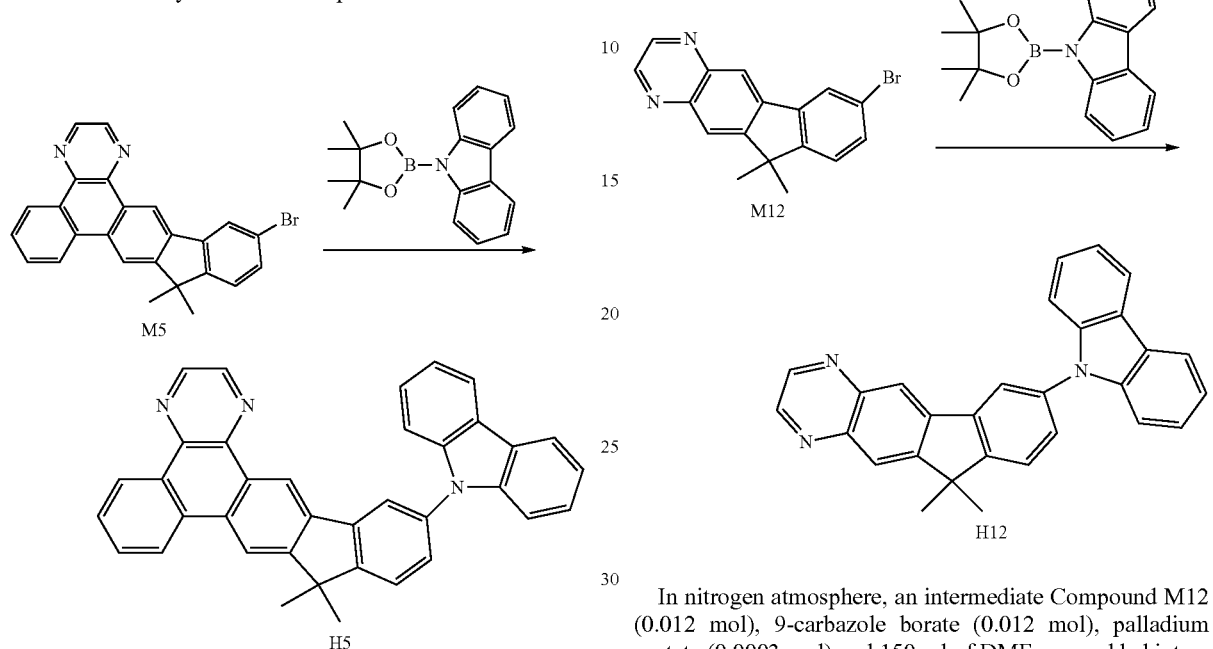

In nitrogen atmosphere, an intermediate Compound M5 (0.012 mol), 9-carbazole borate (0.012 mol), palladium acetate (0.0003 mol) and 150 ml of DMF were added into a 250 ml round bottom flask, mixed and stirred. After a solution of $K_3PO_4$ (0.045 mol) in water was added, the mixture was refluxed for 10 h at a temperature of 130° C., then naturally cooled to room temperature, and the mixture was filtered and dried in a vacuum oven after adding 100 ml of water. The obtained crude product was further separated and purified through a silica gel column chromatography to obtain Compound H5.

Elemental analysis of the Compound H5 (Molecular Formula $C_{37}H_{25}N_3$): theoretical values: C, 86.86; H, 4.93; N, 8.21; test values: C, 86.86; H, 4.95; N, 8.19. The ESI-MS (m/z) (M+) was obtained by liquid chromatography-mass spectrometry: theoretical value: 511.20; and test value: 511.31.

Example 3

Synthesis of Compound H12

In nitrogen atmosphere, an intermediate Compound M12 (0.012 mol), 9-carbazole borate (0.012 mol), palladium acetate (0.0003 mol) and 150 ml of DMF were added into a 250 ml round bottom flask, mixed and stirred. After a solution of $K_3PO_4$ (0.045 mol) in water was added, the mixture was refluxed for 10 h at a temperature of 130° C., then naturally cooled to room temperature, and the mixture was filtered and dried in a vacuum oven after adding 100 ml of water. The obtained crude product was further separated and purified through a silica gel column chromatography to obtain Compound H12.

Elemental analysis of the Compound H12 (Molecular Formula $C_{29}H_{21}N_3$): theoretical values: C, 84.64; H, 5.14; N, 10.21; and test values: C, 84.64; H, 5.16; N, 10.19. The ESI-MS (m/z) (M+) was obtained by liquid chromatography-mass spectrometry: theoretical value: 411.17, and test value: 411.25.

Example 4

Synthesis of Compound H13

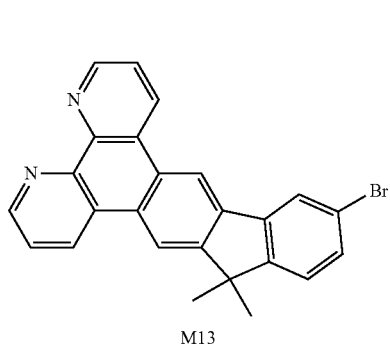 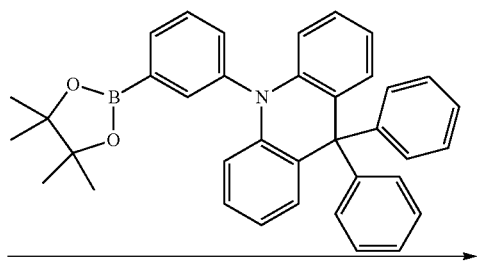

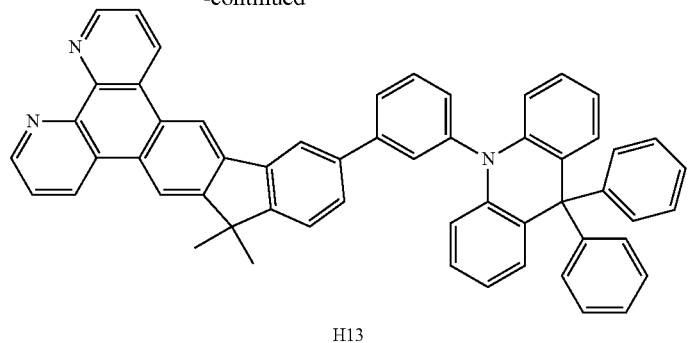

H13

In nitrogen atmosphere, an intermediate Compound M13 (0.012 mol), 9-phenyl-diphenylacridine borate (0.012 mol), palladium acetate (0.0003 mol) and 150 ml of DMF were added into a 250 ml round bottom flask, mixed and stirred. After a solution of K$_3$PO$_4$ (0.045 mol) in water was added, the mixture was refluxed for 10 h at a temperature of 130° C., then naturally cooled to room temperature, and the mixture was filtered and dried in a vacuum oven after adding 100 ml of water. The obtained crude product was further separated and purified through a silica gel column chromatography to obtain Compound H13.

Elemental analysis of the Compound H13 (Molecular Formula C$_{56}$H$_{39}$N$_3$): theoretical values: C, 89.21; H, 5.21; N, 5.57; and test values: C, 89.21; H, 5.23; N, 5.55. The ESI-MS (m/z) (M+) was obtained by liquid chromatography-mass spectrometry: theoretical value, 753.31, and test value, 753.39.

Example 5

Synthesis of Compound H14

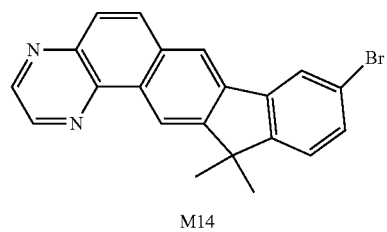

M14

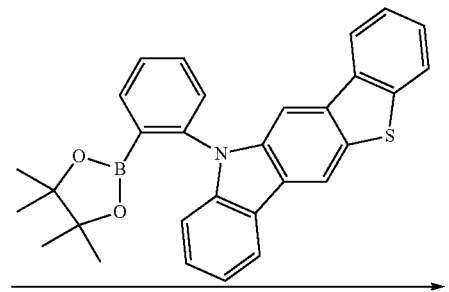

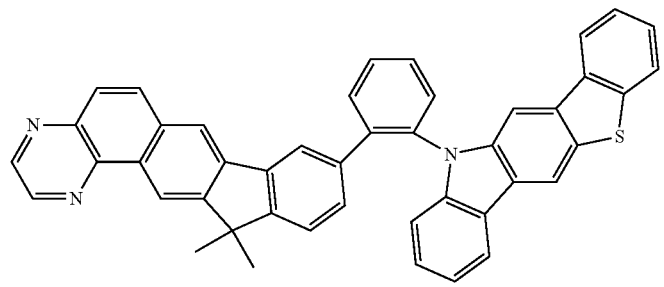

H14

In nitrogen atmosphere, an intermediate Compound M14 (0.012 mol), 9-phenyl-benzothiophenecarbazole borate (0.012 mol), palladium acetate (0.0003 mol) and 150 ml of DMF were added into a 250 ml round bottom flask, mixed and stirred. After a solution of $K_3PO_4$ (0.045 mol) in water was added, the mixture was refluxed for 10 h at a temperature of 130° C., then naturally cooled to room temperature, and the mixture was filtered and dried in a vacuum oven after adding 100 ml of water. The obtained crude product was further separated and purified through a silica gel column chromatography to obtain Compound H14.

Elemental analysis of the Compound H14 (Molecular Formula $C_{45}H_{29}N_3S$): theoretical values: C, 83.95; H, 4.54; N, 6.53; S, 4.98; and test values: C, 83.95; H, 4.53; N, 6.51; S, 5.01. The ESI-MS (m/z) (M+) was obtained by liquid chromatography-mass spectrometry: theoretical value, 643.21, and test value, 643.30.

Example 6

With respect to Compounds H1 to H16, the distribution of the molecular frontier orbitals was optimized and calculated by applying a density functional theory (DFT) and using a Gaussian 09 software with B3LYP/6-31G calculation level.

Figure 2:
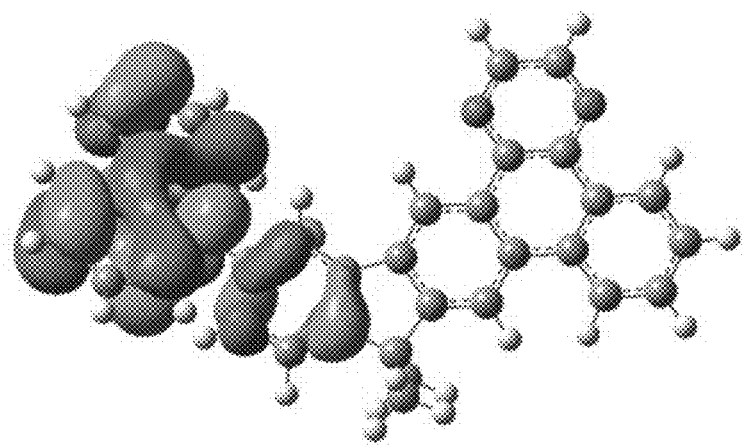
FIG. 2 is a schematic diagram showing highest occupied molecular orbital (HOMO) energy levels of a compound according to an embodiment of the present disclosure.
Figure 3:
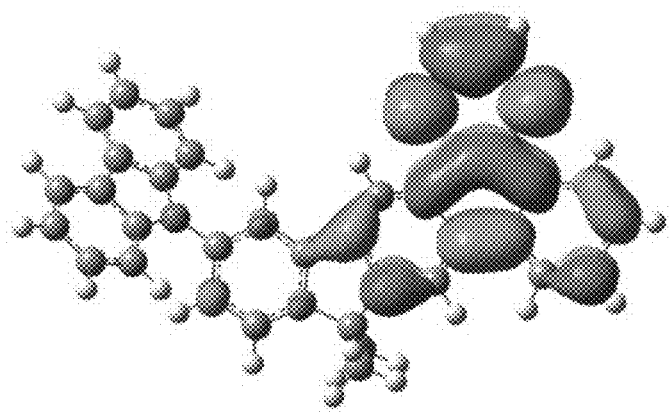
FIG. 3 is a schematic diagram showing lowest unoccupied molecular orbital (LUMO) energy levels of a compound according to an embodiment of the present disclosure.

FIGS. 2 and 3 illustrate orbital configurations of Compound H5. Specifically, FIG. 2 is a diagram of distribution of HOMO energy level of Compound H5, and FIG. 3 is a diagram of distribution of LUMO energy level of Compound H5. It can be seen from FIG. 2 and FIG. 3 that the HOMO and the LUMO of the Compound H5 are distributed on different units, and the presence of the linker provides a complete separation between the electron donor and the electron acceptor, which is conducive to a resonance between the electron donor and the electron acceptor. Thus, the intersystem energy difference $\Delta E_{ST}$ can be reduced, thereby enhancing the reverse intersystem crossing ability.

The relevant data of Compounds H1-16 and comparative examples are shown in Table 1. It can be seen from Table 1 that the compounds according to the present disclosure each has a triplet energy level of greater than 2.70 eV, which is higher than that of the Comparative Compound L1. Meanwhile, all Compounds have relatively small $\Delta E_{ST}$, revealing a small energy level difference between the singlet state and the triplet state, thereby facilitating current carrier transmission between organic functional layers.

The Comparative Compound L1 is has a structure as follow:

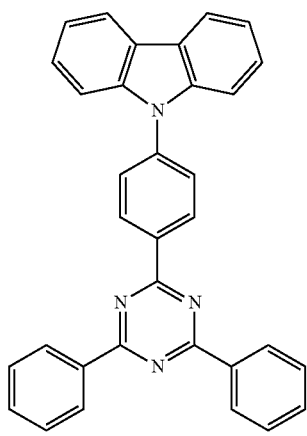

L1

TABLE 1

Performance Data of Compounds H1-H16 and Comparative Compound L1

| Example No. | Compound | HOMO(eV) | LUMO(eV) | $E_T$(eV) | $\Delta E_{ST}$(eV) |
|---|---|---|---|---|---|
| 1 | H1 | −5.56 | −3.05 | 2.72 | 0.19 |
| 2 | H2 | −5.45 | −3.10 | 2.78 | 0.25 |
| 3 | H3 | −5.54 | −3.08 | 2.80 | 0.58 |
| 4 | H4 | −5.72 | −3.02 | 2.79 | 0.40 |
| 5 | H5 | −5.62 | −3.14 | 2.73 | 0.28 |
| 6 | H6 | −5.56 | −3.12 | 2.78 | 0.33 |
| 7 | H7 | −5.48 | −2.98 | 2.80 | 0.10 |
| 8 | H8 | −5.78 | −3.10 | 2.75 | 0.29 |
| 9 | H9 | −5.84 | −3.21 | 2.68 | 0.41 |
| 10 | H10 | −5.65 | −3.08 | 2.73 | 0.23 |
| 11 | H11 | −5.74 | −3.05 | 2.82 | 0.14 |
| 12 | H12 | −5.78 | −3.08 | 2.79 | 0.45 |
| 13 | H13 | −5.65 | −3.12 | 2.84 | 0.29 |
| 14 | H14 | −5.77 | −3.17 | 2.79 | 0.25 |
| 15 | H15 | −5.62 | −3.21 | 2.82 | 0.10 |
| 16 | H16 | −5.74 | −3.04 | 2.75 | 0.22 |
| Comparative Example 1 | L1 | −5.5 | −2.0 | 2.65 | 0.35 |

In Table 1, $E_T$ represents a triplet energy level, and $\Delta E_{ST}$ represents an energy difference between a singlet state and a triplet state.

As can be seen from Table 1, the Compounds H1, H2, H3, H4, H6, H7, H8, H9, H11, and H13 have excellent electron donating ability due to their substituents based on acridinyl, when compared with the Compound L1 of Comparative Example 1. The electron donating ability of the substituent can be effectively adjusted by changing Z atom, which facilitates adjusting light-emitting position. Since Compounds H5, H12, H14, and H15 contain substituents based on carbazolyl, and their electron donating ability is not too strong, the energy difference between HOMO and LUMO may be greater, the band gap is relatively wide, and the emission spectrum shows a blue light emission. Meanwhile, the substituents based on carbazolyl are further fused with another ring, which results in a higher degree of conjugation and a large steric hindrance, so that the molecule has better luminescence performance. The Compounds H10 and H16 contain substituents of diphenylamino group or its derivative, so that electron donating ability of the electron donating group is in the middle between the electron donating ability of the carbazolyl and the electron donating ability of the acridinyl. Therefore, the Compounds H10 and H16 have a relatively strong electron donating ability, and have a structure exhibiting a relatively high steric hindrance, which leads to a small energy difference and a large external quantum efficiency.

A second aspect of the present disclosure provides an organic light-emitting display device. The organic light-emitting display device includes an anode, a cathode, and a light-emitting layer disposed between the anode and the cathode. A host material of the light-emitting layer is selected from the group consisting of nitrogen heterocycle fused ring-indene compounds according to the present disclosure, and combinations thereof.

According to some embodiments of the present disclosure, in the organic light-emitting display device, the light-emitting material of the light-emitting layer is a red light-emitting material, a green light-emitting material, or a blue light-emitting material.

In the organic light-emitting display device provided by the present disclosure, the anode can be made of metal, such as copper, gold, silver, iron, chromium, nickel, manganese, palladium, platinum, and alloys thereof. The anode also can be made of metal oxide, such as indium oxide, zinc oxide, indium tin oxide (ITO), indium zinc oxide (IZO), and the like. The anode also can be made of a conductive polymer, such as polyaniline, polypyrrole, poly(3-methylthiophene) and the like. In addition to the anode material mentioned above, the anode also can be made of any suitable material selected from the anode materials known in the related art, and combinations thereof, as long as the material of the anode is conductive to injecting holes.

In the organic light-emitting display device provided by the present disclosure, the cathode can be made of metal, such as aluminum, magnesium, silver, indium, tin, titanium, etc., or alloys thereof. The cathode also can be made of multiple-layer metal material, such as LiF/Al, LiO$_2$/Al, BaF$_2$/Al, and the like. In addition to the cathode materials listed above, the cathode also can be made of any suitable material selected from the cathode material known in the related art, and combinations thereof, as long as the material of the cathode is conductive to injecting holes.

The organic thin layer in the organic light-emitting display device includes at least one light-emitting layers (EML), and may further include other functional layers, such as a hole injection layer (HIL), a hole transmission layer (HTL), an electron blocking layer (EBL), a hole barrier layer (HBL), an electron transmission layer (ETL), or an electron injection layer (EIL).

In the present disclosure, the organic light-emitting display device can be manufactured by following steps: forming an anode on a transparent or opaque smooth substrate, forming an organic thin layer on the anode, and further forming a cathode on the organic thin layer. The organic thin layer can be formed by a known method such as vapor deposition, sputtering, spin coating, dipping, ion plating, and the like.

In the present disclosure, the organic light-emitting display device can be an OLED, which can be used in an organic light-emitting display device. The organic light-emitting display device may be any display screen of various smart devices, such as a display screen of mobile phone, computer, liquid crystal television, smart watch, a smart car display panel, a virtual reality (VR) or augmented reality (AR) helmet display screen, etc.

The following Example 7 is an illustrative example for explaining technical effect achieved by the nitrogen heterocycle fused ring-indene compound according to the present disclosure in a practical application.

Example 7

Figure 4:
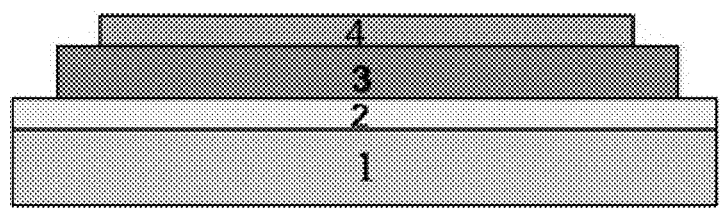
FIG. 4 is a structural schematic diagram of an organic light-emitting component according to an embodiment of the present disclosure.

The structure of the organic light-emitting component according to this example is shown in FIG. 4, which includes a substrate 1 made of glass or other suitable material (e.g., plastic material), a first electrode 2 of a transparent electrode such as ITO or IGZO, an organic functional layer 3 including one or more layers of organic film layer, and a second electrode 4 formed by a metal cathode. The first electrode 2 is interchangeable with the second electrode 4, i.e., the first electrode 2 is a metal cathode, and the second electrode 4 is a transparent electrode such as ITO or IGZO.

An organic electroluminescent component is manufactured by using vacuum vapor deposition.

ITO/hole injection layer (thickness: 10 nm; material: molybdenum trioxide MoO$_3$)/hole transmission layer (thickness: 80 nm; material: TAPC)/light-emitting layer (thickness: 30 nm: material: Compound H5 and Ir(Ppy)$_3$, 100:10 by weight)/electron transmission layer (thickness: 40 nm; material: TPBI)/electron injection layer (thickness: 1 nm; material: LiF)/Al.

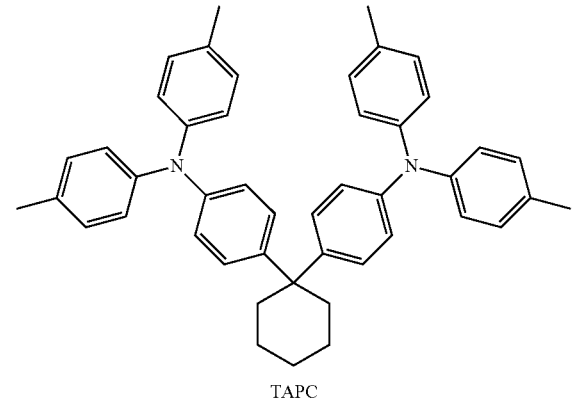

TAPC

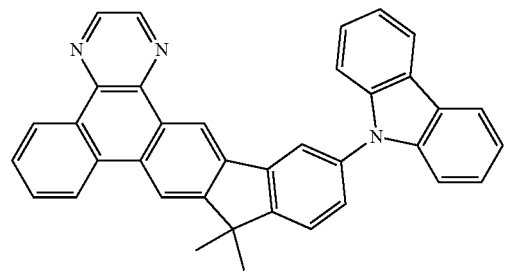

H5

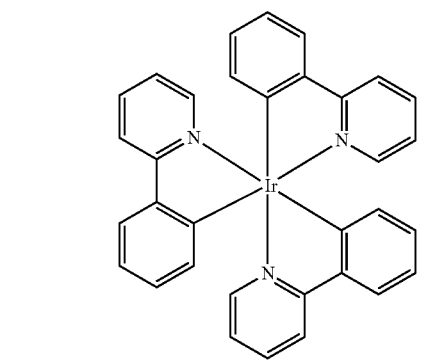

Ir(pyy)$_3$

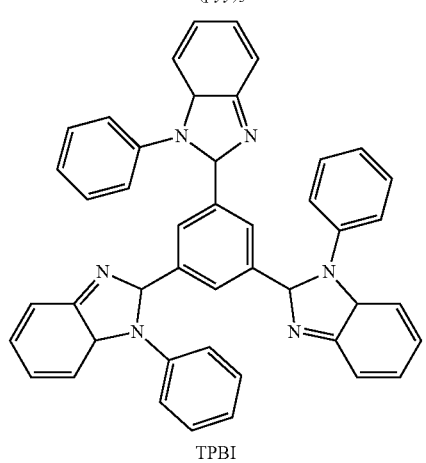

TPBI

The manufacturing process is described as follows:

An ITO transparent electrode having a thickness of 150 nm was washed with alkali, pure water sequentially, then dried and subjected to an ultraviolet-ozone washing to remove organic residues on the surface of the transparent ITO electrode. The cleaned ITO electrode was placed in a vacuum chamber in which the reference pressure was adjusted to $1 \times 10^6$ Torr. Molybdenum trioxide ($MoO_3$) having a film thickness of 10 nm was deposited as a hole injection layer, and subsequently TAPC having a thickness of 80 nm was deposited as a hole transmission layer. After the vapor deposition of the hole transmission material is completed, a light-emitting layer of the OLED light-emitting component having a thickness of 300 nm is manufactured by using the Compound H5 according to the present disclosure as a host material and Ir(ppy) 3 as a dopant in a doping ratio of 1:10 by weight. A hole blocking layer/electron transmission layer (material TPBI) having a thickness of 40 nm and an electron injection layer (material lithium fluoride (LiF)) having a thickness of 1 nm were deposited on the light-emitting layer. Finally, an aluminum (Al) layer having a thickness of 80-100 nm was manufactured as a cathode reflection electrode.

After the OLED light-emitting component was manufactured according to the process described above, it was connected with the anode and the cathode by a known driving circuit for measuring the luminous efficiency, the luminescence spectrum, and the current-voltage characteristics of the device. The structure of the obtained component is shown in FIG. 4. The test results of the obtained component are shown in Table 2.

The organic electroluminescent component also can be manufactured by using a solution method.

The process for manufacturing a non-doped component includes following steps: ultrasonically washing the ITO glass with acetone, alkaline washing solution, ultrapure water, and isopropyl alcohol sequentially for two times, 15 minutes for each time; treating the ITO glass with an ozone cleaner for 15 minutes; spin-coating the glass substrate with 40 nm of PEDOT:PSS solution, and placing the glass substrate in a vacuum oven at 120° C. for 45 minutes for drying; coating the substrate with a solution of the compound according to the present disclosure in o-dichlorobenzene (concentration: 12 mg/mL) so as to form a light-emitting layer having a thickness of 40 nm; transferring the substrate to a vacuum chamber; and vapor-depositing an electron transmission layer (TmPyPb, 50 nm), an electron injection layer (LiF, 0.5-1 nm), and a cathode (Al, 100 nm) to form a complete component.

The process of manufacturing a doped component is the same as that for manufacturing the non-doped component, but further includes several additional steps: preparing solutions of a host material of the light-emitting material and a guest material of the light-emitting material in o-dichlorobenzene (concentration: 12 mg/mL), separately; adding, by a micropipette, 50 uL (5%) of the solution of the guest material into the solution of the host material, and stirring the mixture homogenously by a magnetic stirrer; and then coating the light-emitting layer.

The solution method employed in this embodiment is ink-jet printing method.

Figure 5:
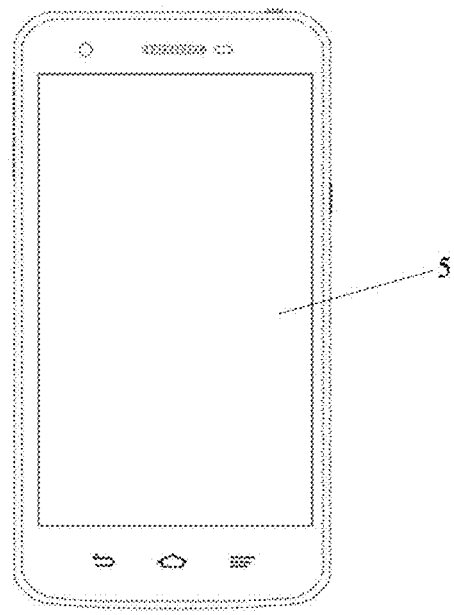
FIG. 5 is a schematic diagram of a mobile phone display screen according to an embodiment of the present disclosure.

The organic light-emitting display device may be a display screen or display panel of mobile phone, computer, liquid crystal television, smart watch, smart car, VR or AR helmet, and other smart devices. FIG. 5 is a schematic diagram of a display screen of a mobile phone, in which the display screen is denoted with number 5.

There are many optional elements and factors of the compound and the organic light-emitting display device according to the present disclosure, so that different embodiments can be obtained by combining the features included in claims of the present disclosure.

Components Manufactured with Vacuum Vapor Deposition Method

Non-doped Component N5', in which Compound H5 is used as light-emitting material, was manufactured and has a structure: ITO (150 nm)/$MoO_3$ (10 nm)/TAPC (80 nm)/H5 (30 nm)/TPBI (40 nm)/LiF (1 nm)/Al (100 nm). Doped Components N1-N16, in which Compounds H1 to H16 are used as light-emitting material respectively and Ir(ppy)$_3$ is used as dopant, were manufactured and each has a structure: ITO (150 nm)/$MoO_3$ (10 nm)/TAPC (80 nm)/H5 (30 nm)/Ir(ppy)$_3$ (50 nm)/TPBI (40 nm)/LiF (1 nm)/Al (100 nm).

The relevant data of the above Components N1-N16 and the Comparative Example N100 are shown in Table 2.

TABLE 2

Performance of Components Manufactured with Vacuum Vapor Deposition Method

| Component | doped/non-doped | V[V] | $E_{L(max)}$(cd $A^{-1}$) | $EQE_{(max)}$ (%) |
|---|---|---|---|---|
| N1 | doped | 4.1 | 19.52 | 14.84 |
| N2 | doped | 3.8 | 19.76 | 14.75 |
| N3 | doped | 3.9 | 19.02 | 15.18 |
| N4 | doped | 4.1 | 20.13 | 15.76 |
| N5' | non-doped | 4.5 | 14.52 | 10.26 |
| N5 | doped | 4.0 | 20.75 | 15.43 |
| N6 | doped | 4.4 | 18.72 | 14.76 |
| N7 | doped | 3.8 | 19.11 | 15.44 |
| N8 | doped | 4.1 | 20.29 | 15.61 |
| N9 | doped | 4.4 | 22.03 | 16.28 |
| N10 | doped | 3.8 | 23.32 | 16.89 |
| N11 | doped | 4.1 | 19.47 | 15.39 |
| N12 | doped | 4.2 | 19.65 | 15.51 |
| N13 | doped | 4.3 | 19.78 | 15.12 |
| N14 | doped | 4.2 | 20.55 | 15.68 |
| N15 | doped | 4.0 | 20.36 | 15.01 |
| N16 | doped | 4.1 | 20.14 | 14.86 |
| N100 | doped | 5.9 | 16.97 | 11.36 |

In Table 2, V represents an operating voltage, $E_{L\ (max)}$ represents a maximum current efficiency, and $EQE_{(max)}$ represents a maximum external quantum efficiency.

It can be seen from Table 2 that the non-doped Component N5', in which Compound H5 is used as a host light-emitting material, achieves a maximum external quantum efficiency of 10.26%. It reveals that the symmetric bonding makes the material exhibit a highly distorted steric configuration and increase steric hindrance. The steric hindrance greatly weakens the triplet exciton quenching caused by π-π stacking, so that the performances of the component can be improved.

It can be seen from Table 2 that the maximum external quantum efficiency of the Component N5 (doped) can reach 15.43%, which is about 45% higher than the EQE(max)(%) of the non-doped component. This may benefit from a higher $E_T$ and a relatively small ΔEST of the Compound H5, so that transmission and recombination of current carriers between the host material and the guest material are facilitated, thereby increasing efficiency of the device. The doped Components N1-N16 each has a EQE(max)(%) above 14.5%, and has a relatively pure blue light emission.

The material described by the present disclosure is applied in the vapor deposition process, so that efficiency is improved, voltage reduction effect is evident, and power consumption of the device is effectively reduced, when compared with the Comparative Example N100.

Example 8

Components Manufactured by Solution Method

Non-doped Component N21', in which Compound H5 is used as light-emitting material, was manufactured and has a structure: ITO (100 nm)/PEDOT:PSS (40 nm)/H5 (40 nm)/TmPyPb (50 nm)/LiF (0.5 nm)/Al (100 nm). Doped Components N17-N32, in which Compounds H1 to H16 are used as light-emitting material respectively and BczVBi is used as dopant, were manufactured and each has a structure: ITO (100 nm)/PEDOT: PSS (40 nm)/H5 (40 nm)/BczVBi (50 nm)/TmPyPb(50 nm)/LiF (0.5 nm)/Al (100 nm).

The relevant data of the Compounds H1 to H16 and the Comparative Example N200 are shown in Table 3.

TABLE 5

Performances of Components Manufactured by Solution Method

| Component | doped/non-doped | V[V] | $E_{L(max)}$(cd A$^{-1}$) | $EQE_{(max)}$ (%) |
|---|---|---|---|---|
| N17 | doped | 4.2 | 16.54 | 12.14 |
| N18 | doped | 4.1 | 16.27 | 12.11 |
| N19 | doped | 4.0 | 17.09 | 12.68 |
| N20 | doped | 4.2 | 17.14 | 13.09 |
| N21' | non-doped | 4.5 | 13.24 | 8.14 |
| N21 | doped | 4.1 | 16.44 | 12.79 |
| N22 | doped | 4.0 | 15.96 | 11.65 |
| N23 | doped | 4.1 | 17.09 | 12.64 |
| N24 | doped | 4.3 | 15.99 | 11.85 |
| N25 | doped | 3.9 | 18.15 | 12.78 |
| N26 | doped | 4.0 | 17.35 | 13.19 |
| N27 | doped | 4.1 | 16.43 | 11.90 |
| N28 | doped | 4.0 | 15.76 | 11.84 |
| N29 | doped | 4.3 | 14.98 | 11.85 |
| N30 | doped | 4.2 | 14.84 | 11.98 |
| N31 | doped | 4.4 | 15.78 | 12.41 |
| N32 | doped | 4.1 | 15.65 | 12.55 |
| N200 | doped | 5.8 | 13.84 | 9.86 |

In Table 3, V represents an operating voltage, $E_{L\ (max)}$ represents a maximum current efficiency, and $EQE_{(max)}$ represents a maximum external quantum efficiency.

It can be seen from Table 3 that the non-doped Component N21', in which Compound H5 is used as a host light-emitting material, achieves a maximum external quantum efficiency of 8.14%. It reveals that the ortho-position substitution makes the material exhibit a highly distorted steric configuration and increase steric hindrance. The steric hindrance greatly weakens the triplet exciton quenching caused by π-π stacking, so that the performances of the component can be improved.

It can be seen from Table 3 that the maximum external quantum efficiency of the Component N21 (doped) can reach 12.79%, which is about 40% higher than the EQE (max)(%) of the non-doped component. This may benefit from a higher $E_T$ and a relatively small ΔEST of the Compound H5, so that transmission and recombination of current carriers between the host material and the guest material are facilitated, thereby increasing efficiency of the device. The doped Components N17-N32 each has a EQE (max)(%) above 11.5%, and has a relatively pure blue light emission.

The material described by the present disclosure is applied in the solution method, so that efficiency is improved, voltage reduction effect is evident, and power consumption of the device is effectively reduced, when compared with the Comparative Example N200.

The above embodiments of the present disclosure are several preferred embodiments, but not intended to limit the scope of the claims. Any change and modification can be made by those skilled in the art without departing from the scope of the present application. The scope of protection is defined by the claims.

What is claimed is:

1. A nitrogen heterocycle fused ring-indene compound being any one of following compounds:

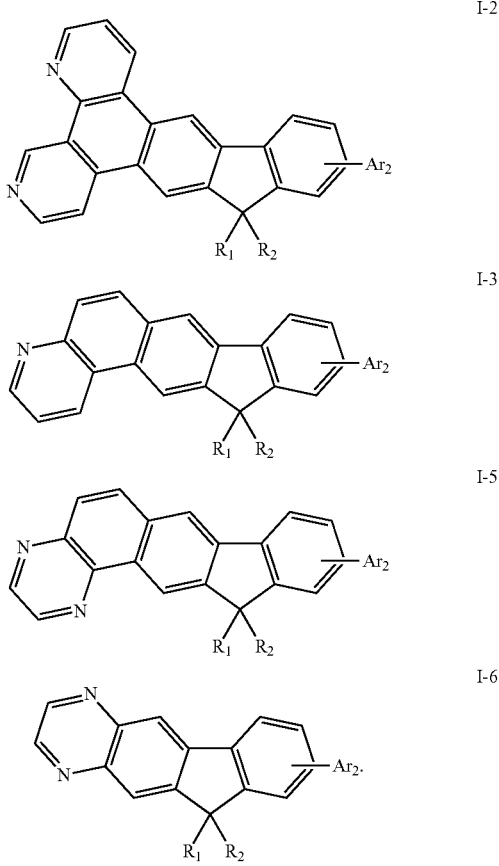

wherein
Ar$_2$ is an electron donor; and
R$_1$ and R$_2$ are independently selected from the group consisting of hydrogen, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

2. The nitrogen heterocycle fused ring-indene compound according to claim 1, wherein R$_1$ and R$_2$ are each methyl.

3. The nitrogen heterocycle fused ring-indene compound according to claim 1, wherein Ar$_2$ is selected from the group consisting of substituted or unsubstituted C1-C20 alkyl, substituted or unsubstituted silicylene, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

4. The nitrogen heterocycle fused ring-indene compound according to claim 1, wherein Ar₂ is any one of following groups:

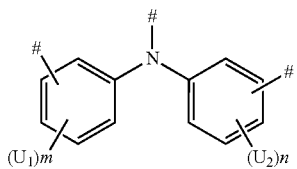

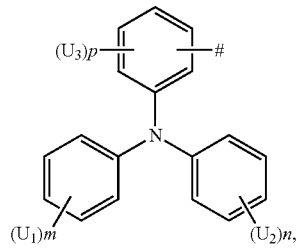

wherein m, n and p are integers independently selected from 0, 1, 2 and 3;

U₁, U₂ and U₃ are independently selected from the group consisting of hydrogen, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C₃₀ fused aryl; and # indicates a bonding position to which a benzene ring in the compounds I-2, I-3, I-5, or I-6 is bonded.

5. The nitrogen heterocycle fused ring-indene compound according to claim 4, wherein Ar₂ is any one of following groups:

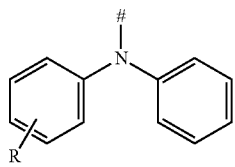

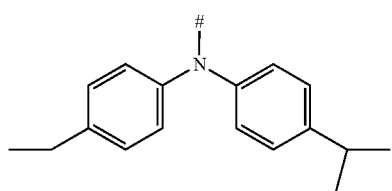

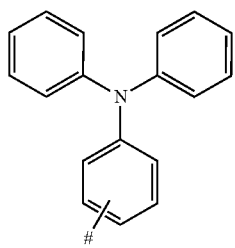

-continued

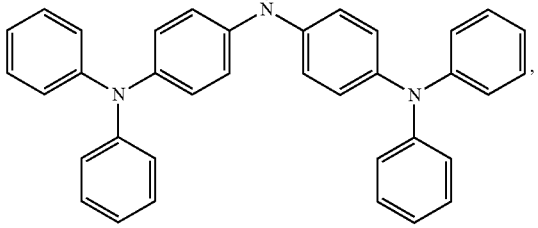

wherein R is selected from the group consisting of hydrogen, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl.

6. The nitrogen heterocycle fused ring-indene compound according to claim 1, wherein Ar₂ is any one of following groups:

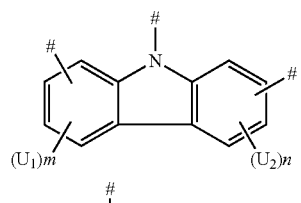

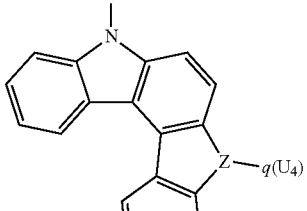

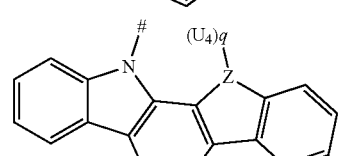

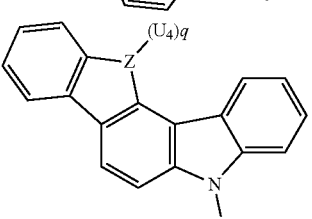

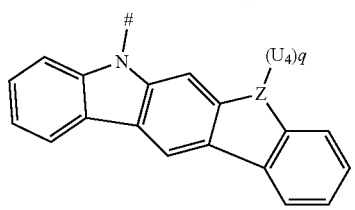

-continued

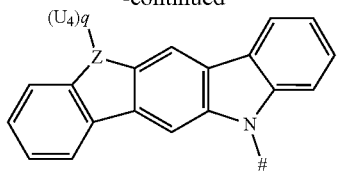

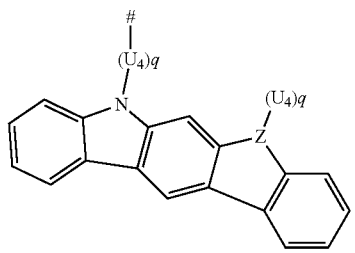

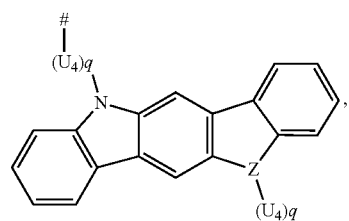

wherein Z is selected from a group consisting of carbon atom, nitrogen atom, oxygen atom, sulfur atom, and silicon atom;

q is an integer selected from 0, 1, 2 and 3;

$U_4$ is selected from the group consisting of hydrogen atom, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl;

when Z is oxygen or sulfur, q=0; and # indicates a bonding position to which a benzene ring in the compounds I-2, I-3, I-5, or I-6 is bonded.

7. The nitrogen heterocycle fused ring-indene compound according to claim 6, wherein $Ar_2$ is any one of following groups:

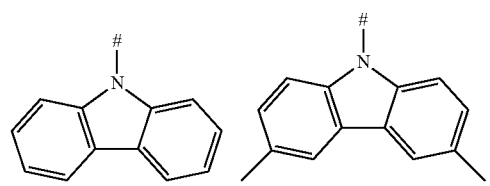

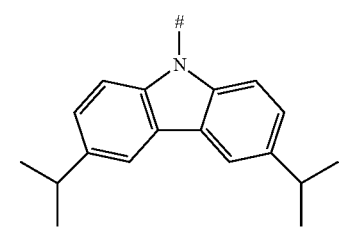

-continued

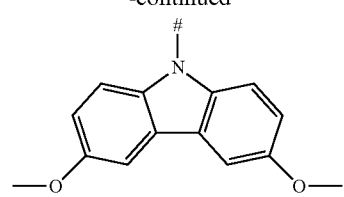

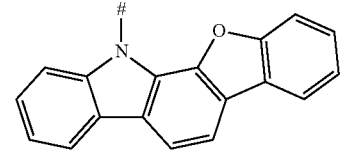

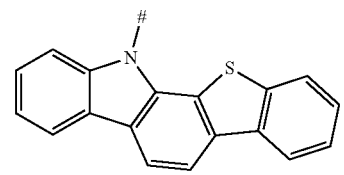

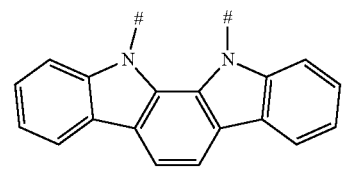

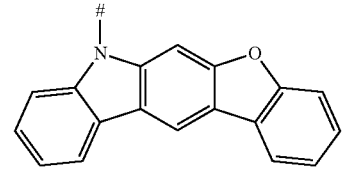

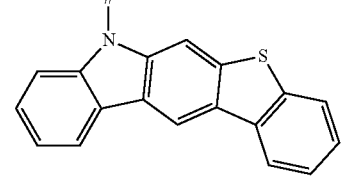

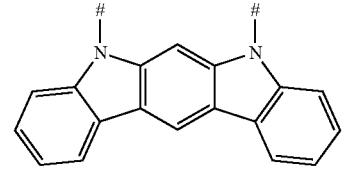

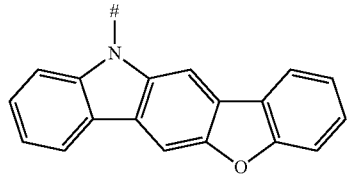

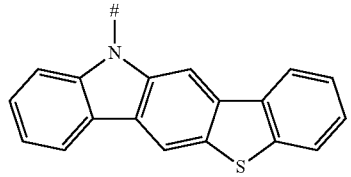

-continued

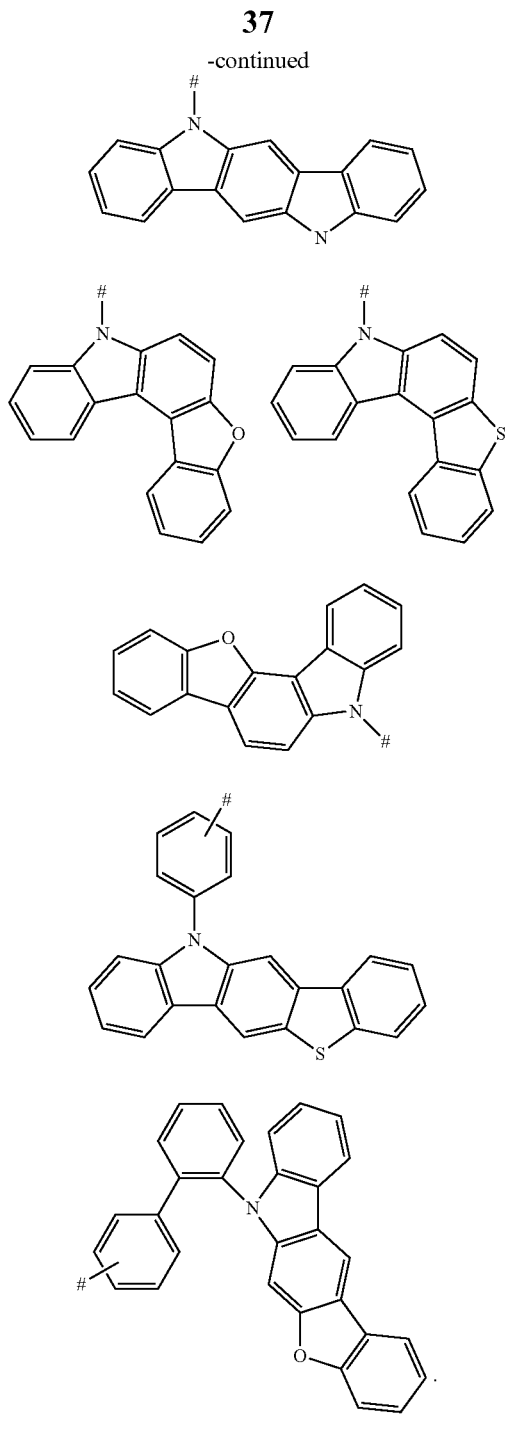

8. The nitrogen heterocycle fused ring-indene compound according to claim 1, wherein Ar2 is any one of following groups:

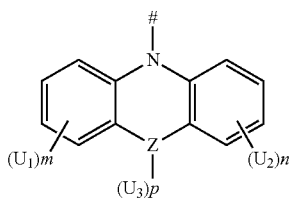

-continued

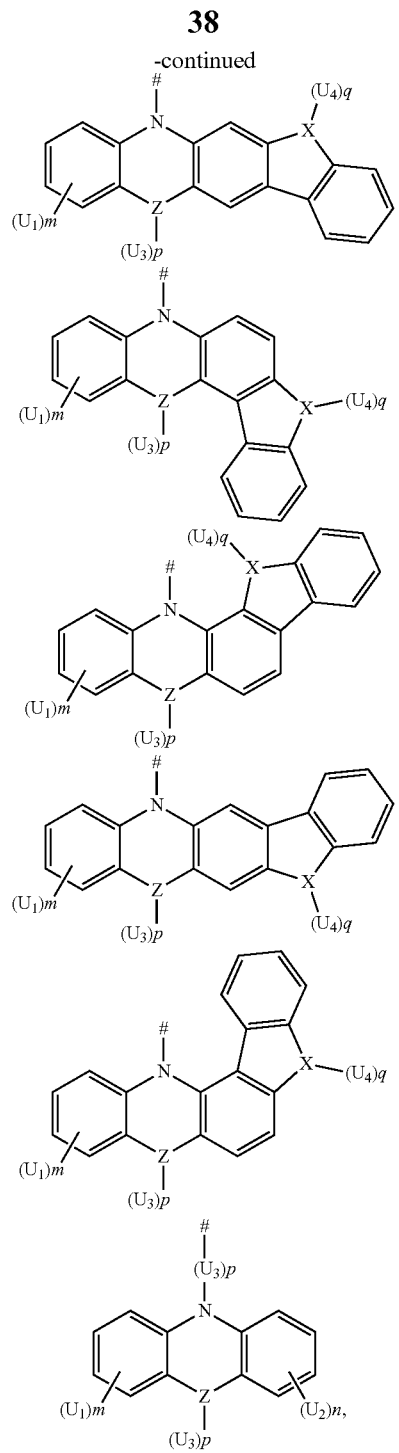

wherein Z is selected from the group consisting of carbon, nitrogen, oxygen, sulfur, and silicon;
X is selected from the group consisting of carbon, nitrogen, oxygen, and sulfur;
m, n, p and q are integers independently selected from 0, 1, 2 and 3;
$U_1$, $U_2$, $U_3$ and $U_4$ are independently selected from the group consisting of hydrogen, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl;

when Z or X is oxygen or sulfur, p or q is 0; and

\# indicates a bonding position to which a benzene ring in the compounds I-2, I-3, I-5, or I-6 is bonded.

9. The nitrogen heterocycle fused ring-indene compound according to claim 8, wherein $Ar_2$ is any one of following groups:

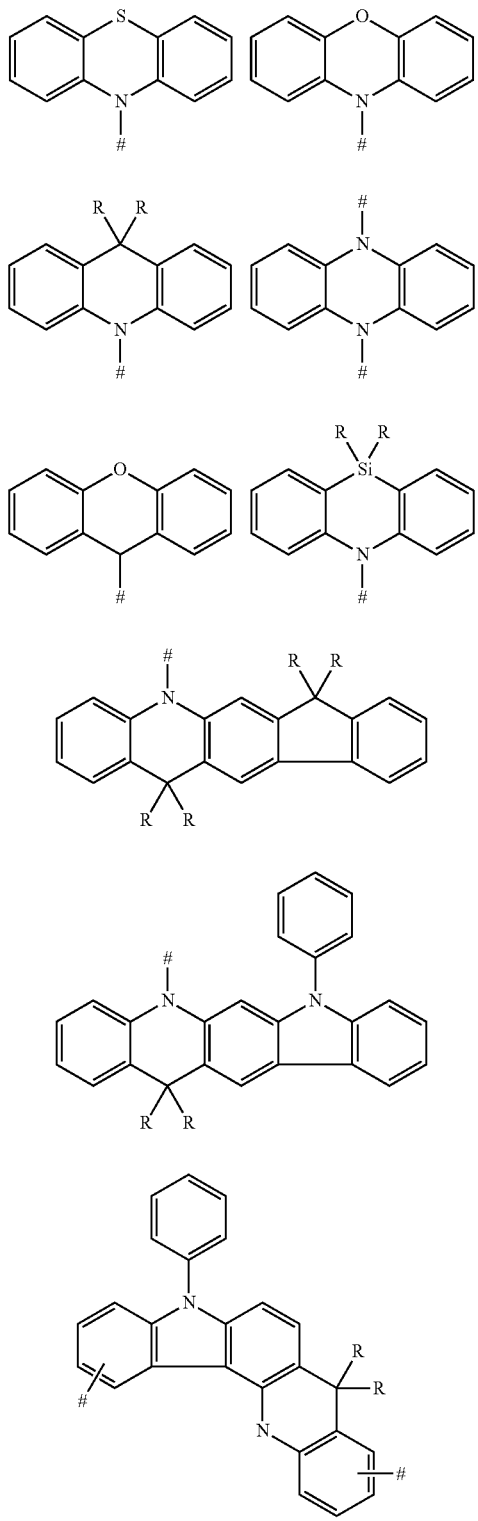

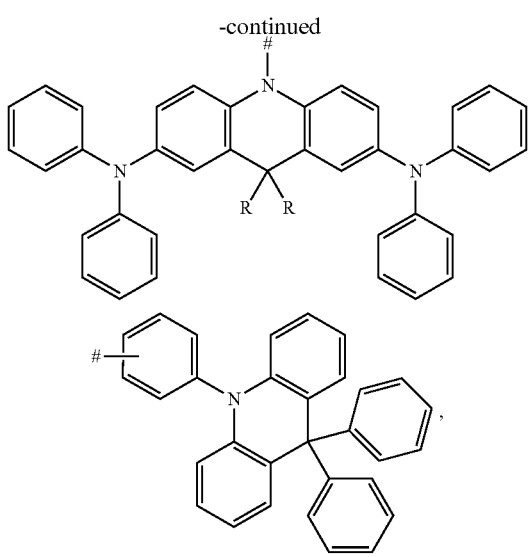

wherein R is selected from the group consisting of hydrogen atom, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

10. The nitrogen heterocycle fused ring-indene compound according to claim 1, wherein $Ar_2$ is any one of following groups:

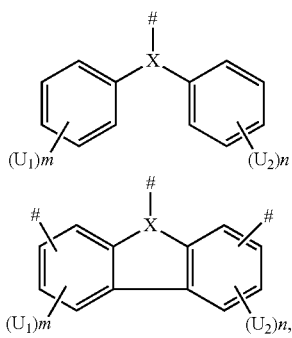

wherein X is selected from the group consisting of oxygen atom, sulfur atom, and silicon atom;

m and n are integers independently selected from 0, 1, 2 and 3;

$U_1$ and $U_2$ are independently selected from the group consisting of hydrogen, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl; and \# indicates a bonding position to which a benzene ring in the compounds I-2, I-3, I-5, or I-6 is bonded.

11. The nitrogen heterocycle fused ring-indene compound according to claim 10, wherein $Ar_2$ is any one of following groups:

12. The nitrogen heterocycle fused ring-indene compound according to claim 1, wherein Ar₂ is any one of following groups:

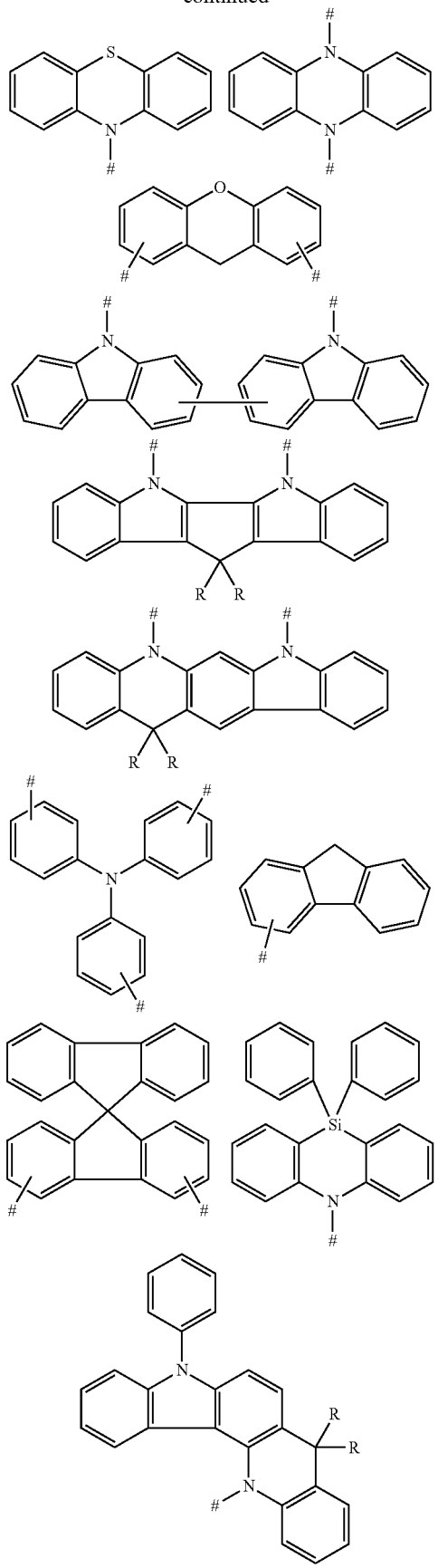

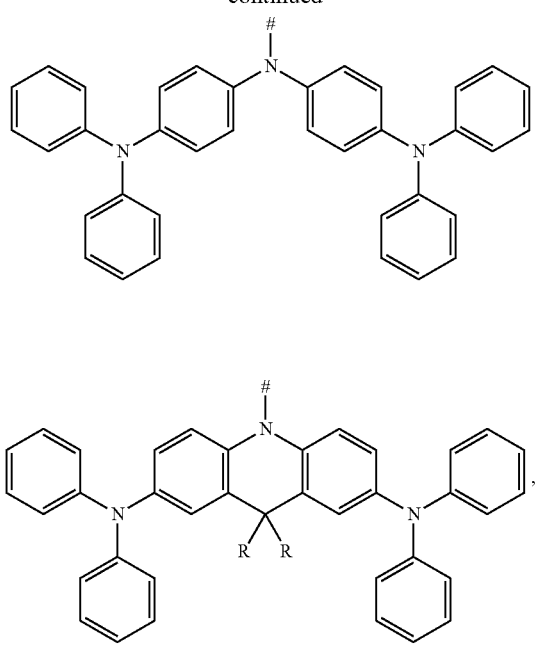

wherein R is selected from the group consisting of hydrogen atom, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

13. The nitrogen heterocycle fused ring-indene compound according to claim 1, wherein the nitrogen heterocycle fused ring-indene compound is any one of following compounds:

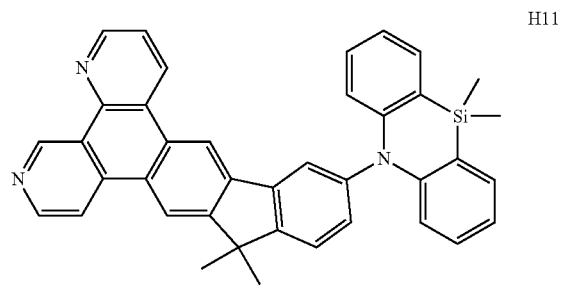

H11

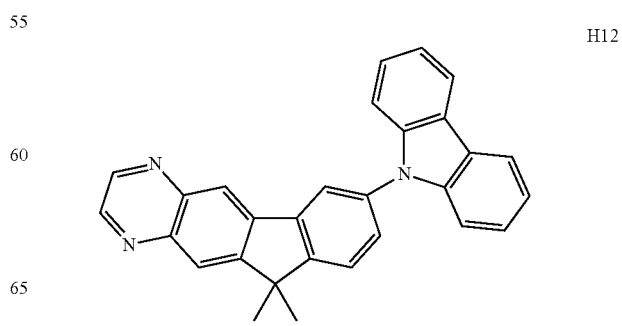

H12

-continued

H13

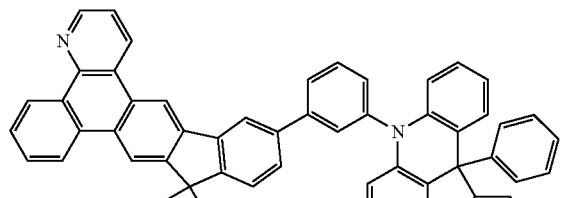

H14

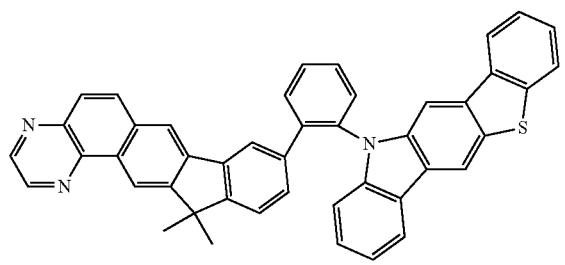

H15

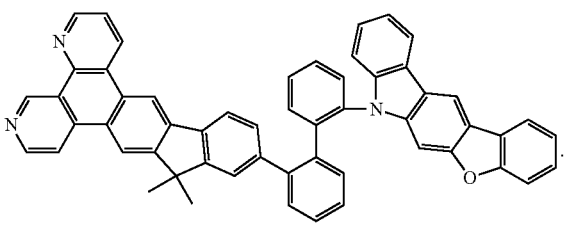

14. An organic light-emitting display device, comprising
an anode;
a cathode; and
a light-emitting layer disposed between the anode and the cathode,
wherein a host material or a guest material of the light-emitting layer is selected from the group consisting of nitrogen heterocycle fused ring-indene compounds, and combinations thereof, the nitrogen heterocycle fused ring-indene compound is any one of following compounds:

I-2

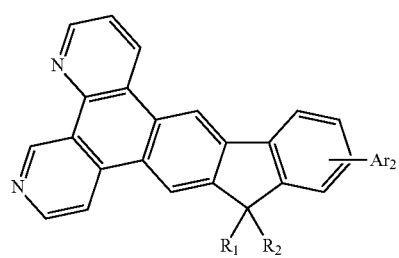

I-3

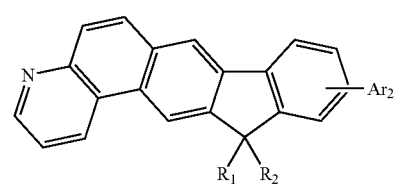

I-5

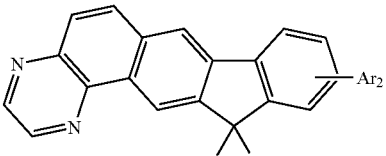

I-6

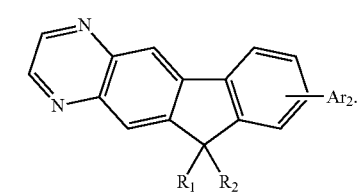

wherein
$Ar_2$ is an electron donor; and
$R_1$ and $R_2$ are independently selected from the group consisting of hydrogen atom, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

15. The organic light-emitting display device according to claim 14, wherein $Ar_2$ is selected from the group consisting of substituted or unsubstituted C1-C20 alkyl, substituted or unsubstituted silicylene, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

16. The organic light-emitting display device according to claim 14, wherein $Ar_2$ is any one of following groups:

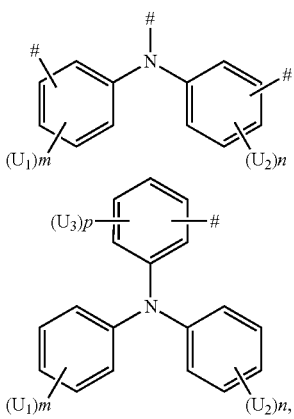

wherein m, n and p are integers independently selected from 0, 1, 2 and 3;
$U_1$, $U_2$ and $U_3$ are independently selected from the group consisting of hydrogen atom, substituted or unsubstituted C1-C30 alkyl, substituted or unsubstituted silicylene, substituted or unsubstituted C3-C20 cycloalkyl, substituted or unsubstituted C1-C30 alkoxy, substituted or unsubstituted C6-C30 aryl, and substituted or unsubstituted C10-C30 fused aryl; and
# indicates a bonding position to which a benzene ring in the compounds I-2, I-3, I-5, or I-6 is bonded.

17. The organic light-emitting display device according to claim 14, further comprising a hole injection layer, a hole transmission layer, an electron blocking layer, a hole blocking layer, an electron transmission layer, an electron injection layer, or any combination thereof.

18. The organic light-emitting display device according to claim 17, wherein the electron transmission layer or the hole transmission layer is made of a material selected from the group consisting of nitrogen heterocycle fused ring-indene compounds, and combinations thereof, the nitrogen heterocycle fused ring-indene compounds is any one of following compounds:

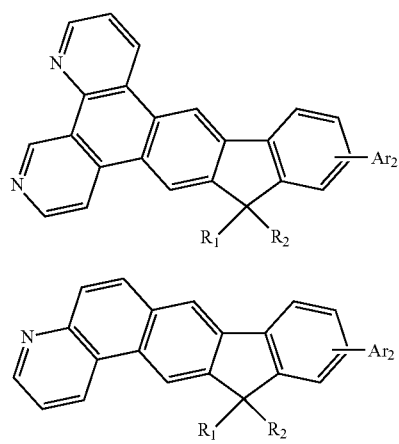

I-2

I-3

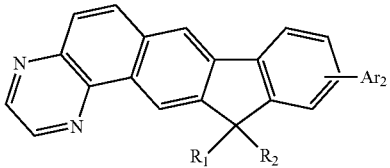

I-5

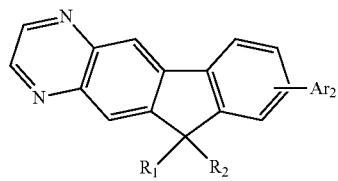

I-6 wherein

Ar₂ is an electron donor; and

R₁ and R₂ are independently selected from the group consisting of hydrogen, substituted or unsubstituted C1-C20 alkyl, substituted or unsubstituted C3-C20 cycloalkyl, substituted or unsubstituted C1-C20 alkoxy, substituted or unsubstituted C3-C20 heterocyclyl, substituted or unsubstituted C6-C40 aryl, and substituted or unsubstituted C5-C40 heteroaryl.

\* \* \* \* \*

UNITED STATES PATENT AND TRADEMARK OFFICE
CERTIFICATE OF CORRECTION

Page 1 of 1

PATENT NO. : 11,183,643 B2
APPLICATION NO. : 16/212292
DATED : November 23, 2021
INVENTOR(S) : L. Zhang et al.

It is certified that error appears in the above-identified patent and that said Letters Patent is hereby corrected as shown below:

In the Claims

| Column | Line | |
|---|---|---|
| 33 | 33 | In Claim 4, change "$C_{30}$" to -- C30 --. |

Signed and Sealed this
Twenty-ninth Day of November, 2022

Katherine Kelly Vidal
*Director of the United States Patent and Trademark Office*